US008632452B2

(12) United States Patent
Huang et al.

(10) Patent No.: US 8,632,452 B2
(45) Date of Patent: Jan. 21, 2014

(54) PEROXISOME PROLIFERATOR-ACTIVATOR RECEPTOR δ (PPARδ) AND THE DEVELOPMENT OF PREIMPLANTATION EMBRYOS

(75) Inventors: Jaou-Chen Huang, Houston, TX (US); Alfred W-S Wun, Houston, TX (US); Jennifer S. Goldsby, Houston, TX (US); Kenneth Wu, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 1013 days.

(21) Appl. No.: 12/090,060

(22) PCT Filed: Oct. 12, 2006

(86) PCT No.: PCT/US2006/039842
§ 371 (c)(1),
(2), (4) Date: Sep. 19, 2008

(87) PCT Pub. No.: WO2007/047341
PCT Pub. Date: Apr. 26, 2007

(65) Prior Publication Data

US 2009/0156890 A1 Jun. 18, 2009

Related U.S. Application Data

(60) Provisional application No. 60/725,928, filed on Oct. 12, 2005.

(51) Int. Cl.
*A61B 17/43* (2006.01)
*C12N 5/06* (2006.01)

(52) U.S. Cl.
USPC .............................. 600/35; 435/375; 435/404

(58) Field of Classification Search
None
See application file for complete search history.

(56) References Cited

FOREIGN PATENT DOCUMENTS

WO 2005/026324 A2 3/2005

OTHER PUBLICATIONS

Lim et al. (Genes and Development, 1999, vol. 13, p. 1561-1574 in IDS on Feb. 15, 2010).*

Huang (Human Reproduction, 2004, vol. 19, p. 1856-1860 in IDS on Feb. 15, 2010).*

Berry et al. (Molecular Pharmacology, Apr. 2005, vol. 68, p. 169-178).*

Supplementary Search Report for EPO Application No. 06825808.6, dated Dec. 10, 2009, 10 pages.

Lim Hyunjung et al., "Cyclo-Oxygenase-2-Derived Prostacyclin Mediates Embryo Implantation in the Mouse Via PPARdelta," Genes and Development, Cold Spring Harbor Laboratory Press, Plainview, NY, US, vol. 13, No. 12, Jun. 15, 1999, pp. 1561-1574.

Huang J-C et al., "Prostacyclin Enhances the Implantation and Live Birth Potentials of Mouse Embryos," Human Reproduction, Oxford University Press, GB, vol. 19, No. 8, Aug. 1, 2004, pp. 1856-1860.

Huang Jaou-Chen et al., "Enhanced Hatching of Mouse Embryos by Prostacyclin Corresponded to the Stage-Specific Expression of Prostacyclin Receptor by the Mouse Embryos," Fertility and Sterility, Elsevier Science Inc., New York, NY, US, vol. 80, No. Suppl. 3, Sep. 1, 2003.

Huang J-C et al., "Prostacyclin Enhances Embryo Hatching But Not Sperm Motility," Human Reproduction, Oxford University Press, GB, vol. 18, No. 12, Dec. 1, 2003, pp. 2582-2589.

Huang Jaou-Chen et al., "Human Fallopian Tubes Express Prostacyclin (PGI) Synthase and Cyclooxgenases and Synthesize Abundant PGI" Journal of Clinical Endrocrinology and Metabolishm, Endocrine Society, Chevy Chase, MD, vol. 87, No. 9, Sep. 1, 2002, pp. 4361-4368.

Noorhasan D.J. et al., "Peroxisome Proliferator-Activated Receptor & Ligand Is a Survival Factor of Pre-Implantation Embryo," Fertility and Sterility, Sep. 2005, p. 403.

Huang J-C et al., "Stimulation of Embryo Hatching and Implantation by Prostacyclin and Peroxisome Proliferator-Activated Receptor Delta Activation: Implication in IVF," Human Reproduction, Oxford University Press, GB, vol. 22, No. 3, Mar. 2007, pp. 807-814.

* cited by examiner

*Primary Examiner* — Agnieszka Boesen
(74) *Attorney, Agent, or Firm* — Conley Rose, P.C.

(57) ABSTRACT

Methods and compositions for enhancing development of a preimplantation mammalian embryo and for increasing the live birth potential of an in vitro fertilized mammalian embryo are disclosed. An in vitro method of activating the peroxisome proliferator activated receptor δ (PPARδ) in a preimplantation mammalian embryo comprises culturing an embryo in an embryo culture medium, and upon or after commencement of expression of PPARδ in the cells of the embryo, activating the PPARδ by adding an amount of a PPARδ ligand to said medium effective to bind to PPARδ to deter apoptosis in the cells of the cultured embryo and/or increase proliferation of the cells of the cultured embryo.

9 Claims, 15 Drawing Sheets

| | | | | | |
|---|---|---|---|---|---|
| 2 cell embryo | – | + | – | – | – |
| 8 cell embryo | – | + | + | – | – |
| Morula | – | + | + | + | – |
| Early blastocsyt | – | + | + | + | + |
| Hatching blastocyst | – | + | + | + | + |

L165,041 exposure based on stages of embryo development d

```
                              SEQUENCE LISTING

<160> NUMBER OF SEQ ID NOS: 4

<210> SEQ ID NO 1
<211> LENGTH: 20
<212> TYPE: DNA
<213> ORGANISM: Unknown
<220> FEATURE:
<223> OTHER INFORMATION: Synthetic primer sequence

<400> SEQUENCE: 1

ttctagagcc cgcagaatgg                                                   20


<210> SEQ ID NO 2
<211> LENGTH: 21
<212> TYPE: DNA
<213> ORGANISM: Unknown
<220> FEATURE:
<223> OTHER INFORMATION: Synthetic primer sequence

<400> SEQUENCE: 2

gccaagaaca tccccaactt c                                                 21
```

-continued

```
<210> SEQ ID NO 3
<211> LENGTH: 20
<212> TYPE: DNA
<213> ORGANISM: Unknown
<220> FEATURE:
<223> OTHER INFORMATION: Synthetic primer sequence

<400> SEQUENCE: 3

cctggatggc ttctacctgg                                                20


<210> SEQ ID NO 4
<211> LENGTH: 14
<212> TYPE: PRT
<213> ORGANISM: Unknown
<220> FEATURE:
<223> OTHER INFORMATION: Synthetic sequence reagent for antibody
      production

<400> SEQUENCE: 4

Met Glu Gln Pro Gln Glu Glu Thr Pro Glu Ala Arg Glu Glu
1               5                   10
```

PEROXISOME PROLIFERATOR-ACTIVATOR RECEPTOR δ (PPARδ) AND THE DEVELOPMENT OF PREIMPLANTATION EMBRYOS

This application is the U.S. National Stage under 35 U.S.C. §371 of International Patent Application No. PCT/US2006/039842 filed Oct. 12, 2006, which claims priority of U.S. Provisional Patent Application No. 60/725,928 filed Oct. 12, 2005.

BACKGROUND OF THE INVENTION

1. Field of the Invention

The present invention generally relates to compositions and methods for in vitro culturing of a mammalian embryo and for enhancing achievement of pregnancy after implantation of the cultured embryo in the uterus of a suitable mammalian host.

2. Description of Related Art

Peroxisome proliferator activated receptor (PPAR) is a group of ligand activated transcription factors. It has three isotypes: PPARα, PPARγ, and PPARδ (also called PPARβ). The three PPARs belong to the nuclear receptor super family (Mangelsdorf et al., 1995), which includes steroid hormone receptor, thyroid hormone receptor, retinoid receptor and a growing number of orphan receptors. Ligand bound PPAR first heterodimerizes with RXR (which is a member of the retinoid receptor subfamily) before binding to the PPAR responsive element in the promoter of PPAR-responsive genes (Willson et al., 2000; Berger et al., 2002).

The roles of PPARα and PPARγ in energy homeostasis and inflammatory responses are suggested by their tissue-specific distribution and their natural ligands (Hihi et al., 2002; Wahli 2002). PPARα is present mainly in liver, brown adipose tissue and skeletal muscle; PPARγ is present mainly in the adipose tissue, macrophages and colon. Natural ligands for PPARα and PPARγ include polyunsaturated fatty acid (such as arachidonic acid and linoleic acid), leukotriene $B_4$ (a product of arachidonic acid via lipoxygenase pathway), oxidized low-density lipoprotein, 9- and 13-hydroxoctadecadienoic acid, and, possibly, 15Δ-prostaglandin $J_2$ (Forman et al., 1997). Synthetic PPARα and PPARγ ligands are used to treat lipid and glucose disorders: fibric acid, a PPARα ligand, is a lipid-lowering agent; thiazolidinedione, a PPARγ ligand, is an insulin sensitizer (Berger et al., 2002).

Although the identity of natural ligand(s) for PPARδ remains an enigma (Braissant et al., 1998), the diverse biological functions of PPARδ have been revealed by synthetic PPARδ ligand and mouse models with targeted PPARδ function (Peters et al., 2000; Barak et al., 2002). The reported functions of PPARδ include lipid homeostasis (Forman et al., 1997), endometrial receptivity (Lim et al., 2000; Ding et al., 2003), inflammation (Lee et al., 2003), wound healing (Michalik et al., 2001; Wahli 2002), myelination of the brain (Peters et al., 2000) and resistance to stress (Hao et al., 2002). Furthermore, PPARδ is implicated in colon cancer (Gupta et al., 2000; Cutler et al., 2003).

Prostacyclin ($PGI_2$) is one of the putative natural ligands for PPARδ. High levels of $PGI_2$ and PPARδ messages are coexpressed at implantation sites in the uterus (Lim et al., 1999). $PGI_2$ analog or synthetic PPARδ ligand restores the loss of endometrial receptivity in cyclooxygenase-2 targeted mice (Lim et al., 1999; Lim et al., 2000). In renal medullary cells, which do not express $PGI_2$ receptor, increased $PGI_2$ production concomitant with enhanced activity of PPARδ response element promotes their survival during hypertonic stress (Hao et al., 2002). Finally, $PGI_2$ is the possible link between non-steroidal anti-inflammatory drugs, which inhibit PG synthesis, and colon cancer prevention (Gupta et al., 2000; Cutler et al., 2003).

The development of preimplantation embryos in vivo is promoted by a coordinated program involving soluble factors from the oviducts and the uterus (Yeung et al., 1992). Prostacyclin ($PGI_2$), one of the factors produced by the oviducts and the uterus via cyclooxygenase-2 (COX-2) pathway, plays a crucial role in embryo development and implementation (Huang et al., 2004a; Huang et al., 2004b; Huang et al., 2003; Lim et al., 1999). Compared with the development of in vivo embryos, the development of cultured embryos such as in vitro fertilized (IVF) embryos is retarded because cultured embryos were deprived of the protective environment of the oviduct (Hardy, 1997). Our recent work showed that supplementing culture media with iloprost, a stable analog of $PGI_2$, enhances mouse blastocyst hatching in vitro (Huang et al., 2003). Furthermore, embryos preconditioned by iloprost show an enhanced potential of implantation and live births when transferred to gestational carriers (Huang et al., 2004b). A source of $PGI_2$, other than the oviducts and uterus, is preimplantation embryos. Blocking the production of endogenous $PGI_2$ by selective COX-2 inhibitors retards embryo hatching (Huang et al., 2004c). Thus, $PGI_2$ is crucial for embryo development in vitro, and its stable analog effectively improves the hatching and implantation of cultured embryos. Although preimplantation embryos express $PGI_2$ receptor and possess functional protein kinase A, $PGI_2$ analog did not increase their cAMP levels (Huang et al., 2003). It remains unclear how $PGI_2$ and its analogs achieve these enhancements.

$PGI_2$ exerts its effects by binding to a G-protein coupled prostaglandin receptor (IP) and/or peroxisome proliferator-activated receptor δ (PPARδ) (Forman et al., 1997; Namba et al., 1994). The inhibition of platelet aggregation and the relaxation of smooth muscle cells by $PGI_2$ are mediated by IP receptors via the cyclic AMP-dependent kinase (PKA) pathway (Namba et al., 1994). PPARδ has been implicated in cell protection by $PGI_2$ (Adderley and Fitzgerald, 1999; Hao et al., 2002; Tan et al., 2001). IP null mice have increased propensity for thrombosis (Cheng et al., 2002); PPARδ null mice exhibit reproductive defects (Barak et al., 2002; Cheng et al., 2002).

It has been previously reported that embryos cultured in medium supplemented with $PGI_2$ analog showed enhanced hatching (Huang et al., 2003), implantation and live birth (Huang et al., 2004; International Patent Application PCT/US2004/029167 (Huang et al.) entitled "Method and Composition for Enhancing In Vitro Embryo Development By Supplementing Culture Medium with Prostaglandin or a Prostaglandin Analog"; and U.S. patent application Ser. No. 11/370,152 (Huang et al.) entitled "Enhancement of Mammalian Embryo Development," the disclosures of which are hereby incorporated herein by reference. Ways to further increase IVF success by improving in vitro development of preimplantation embryos to enhance their potential for being successful implanted in utero, and to increase the rate of live births from such embryos continue to be sought.

SUMMARY OF THE INVENTION

It is disclosed that preimplantation embryos express PPARδ, and that ablation of PPARδ results in decreased cell proliferation and irreversible developmental delay. Activation of PPARδ by synthetic ligand was demonstrated to increase proliferation of embryonic cells, to enhance embryo hatching in-vitro, and to enhance implantation of cultured embryos. PPARδ represents a new therapeutic target to improve IVF outcome. These discoveries are expected to be especially useful in such medical technologies as in vitro fertilization.

In accordance with certain embodiments of the present invention, an in vitro method of activating the peroxisome proliferator activated receptor δ (PPARδ) in a preimplantation mammalian embryo is provided which comprises culturing an embryo in an embryo culture medium, and, upon or after commencement of expression of PPARδ in the cells of the embryo, activating the PPARδ by binding a PPARδ ligand to the expressed PPARδ to deter apoptosis in the cells of the cultured embryo and/or increase proliferation of the cells of the cultured embryo.

In certain embodiments, binding PPARδ ligand to the expressed PPARδ enhances hatching of the embryo. In certain embodiments, the method further comprises supplementing the medium with a prostaglandin, or analog thereof, in an amount effective to promote complete hatching of the embryo. In certain embodiments, the ligand comprises at least one natural or synthetic ligand other than a prostaglandin or analog thereof.

In certain embodiments, ligand is added to the medium at the morula-stage or later in the development of said embryo. In some embodiments, the ligand comprises L1165,041 and in some embodiments the ligand comprises GW501516.

In certain embodiments, the method yields an embryo with increased in vivo implantation potential. In certain embodiments, the method yields an embryo with enhanced potential for establishment of a viable pregnancy.

Also provided in accordance with the present invention is a method of increasing the live birth potential of an in vitro fertilized mammalian embryo, which comprises (a) enhancing development of the embryo according to an above-described method, wherein said supplementing of the medium with a synthetic PPARδ ligand yields a PPARδ ligand-treated embryo; (b) introducing the PPARδ ligand-treated embryo into the uterus of a mammal; and (c) allowing the introduced embryo to become implanted in said uterus, wherein the ability of the embryo to hatch and become implanted in the uterus of the host is enhanced compared to that of an embryo that is not cultured in the presence of said synthetic PPARδ ligand. In some embodiments, step (b) comprises transferring a blastocyst-staged or earlier-staged PPARδ ligand-treated embryo to the uterus.

Still further provided in accordance with the present invention is an improved embryo culture medium for in vitro development of a mammalian embryo wherein the improvement comprises an amount of peroxisome proliferator activated receptor δ (PPARδ) ligand in the medium effective to increase proliferation of embryonic cells, wherein said ligand is other than a prostaglandin or an analog thereof. In certain embodiments, the amount of PPARδ ligand in the medium is effective to promote complete hatching of an embryo, when the embryo is cultured in the medium. In certain embodiments, the medium further comprises an amount of a prostaglandin, or analog thereof, effective to promote complete hatching of a cultured embryo, when the embryo is cultured in the medium.

Still another embodiment of the present invention provides the use of a PPARδ ligand, as defined above, that binds to PPARδ in an in vitro cultured embryo cell expressing PPARδ, in the manufacture of a medicament for activating PPARδ to deter apoptosis in the embryo cells and/or to increase proliferation of the embryo cells, to enhance the live birth potential of an in vitro fertilized mammalian embryo after introduction into the uterus of a mammal. These and other embodiments, features and advantages of the present invention will become apparent with reference to the following description and drawings.

DETAILED DESCRIPTION OF THE PREFERRED EMBODIMENTS

Figure 1A:
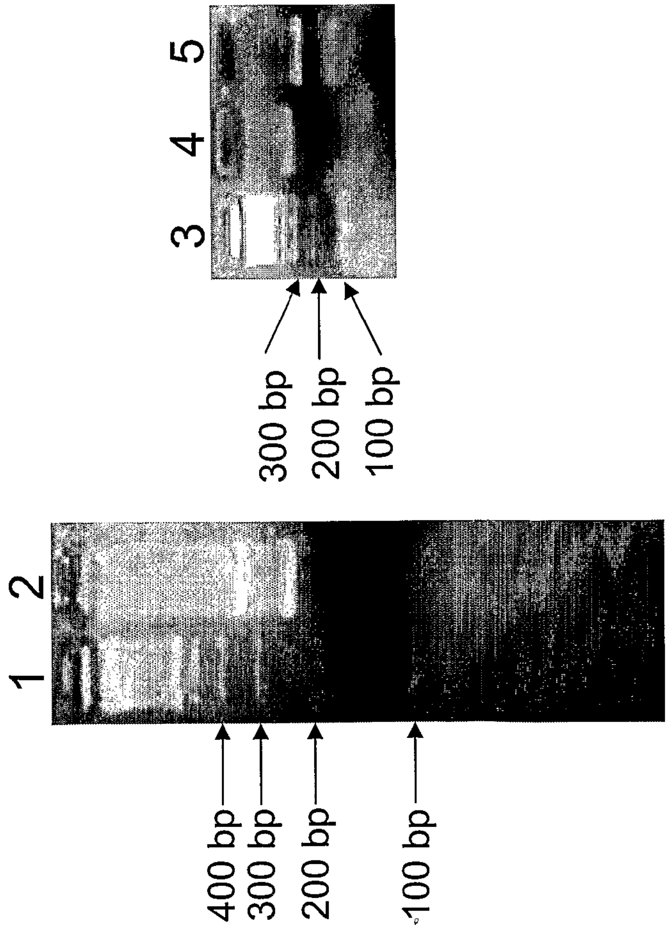
FIG. 1. Mouse embryos express peroxisome proliferator-activated receptor δ (PPARδ). (a) Total RNA from 20 mouse blastocysts were reverse transcribed and amplified by PCR using primers based on exons 5 and 6 of mouse PPARδ sequences. The PCR products were electrophoresed on a 2% agarose gel. The expected size of the amplicon was 334 base pairs (lane 2). The ~330 base pairs amplicon was eluted and digested by the restriction enzyme SST1. The undigested and the digested DNA (lanes 4 and 5, respectively) were electrophoresed on a 3% agarose gel. The two fragments in lane 5 are of expected size: 95 and 239 base pairs. (Lanes 1 and 3 are 100 base pair ladder). (b) Total cell lysate of sixty mouse blastocysts (lane 1) and liver (lane 2, 30 μg) were separated on a poly-acrylamide gel and electro-transferred to a nitrocellulose membrane. The membrane was probed with an affinity purified, polyclonal rabbit antibody against a synthetic peptide based on mouse PPARδ sequence and visualized by chemi-fluorescence. The immuno-reactive protein migrated to the location of expected molecular weight (~58 kDa).

I. Enhancement of Embryo Hatching and Reduced Apoptosis of Embryonic Cells

Oviduct-derived prostacyclin optimizes the development of preimplantation embryos and enhances their potentials of hatching, implantation and live birth. The signaling of prostacyclin in the preimplantation embryos is not clear. To explore the possibility that peroxisome proliferator activated receptor δ (PPARδ) may mediate the effects of PGI2 in the preimplantation embryos (e.g., PGI2 signaling), the expression of PPARδ in preimplantation embryos was investigated, and it was activated by synthetic PPARδ ligand. The preimplantation embryos' responses to synthetic PPARδ ligand were assessed based on complete embryo hatching and apoptosis of embryonic cells. To reveal the role of PPARδ in the development of preimplantation embryos, the development of PPARδ knockout (PPARδ targeted (PPARδ−/−)) and wild type embryos were compared. It was found that preimplantation mouse embryos express PPARδ, as determined by RT/PCR and Western blot analysis, as described in more detail below. Its activation by synthetic ligand enhanced embryo hatching and reduced apoptosis. Synthetic PPARδ ligand reduced apoptosis, increased proliferation, and enhanced embryo hatching in a concentration-dependent manner (ED50=21 nM). Ablation of PPARδ by gene targeting led to decreased cell proliferation and irreversible developmental delay in the preimplantation embryos. Thus, preimplantation embryos express PPARδ, which is critical to normal development and embryonic cell proliferation. The activation of PPARδ by synthetic ligand enhances embryo hatching in-vitro. In light of these representative studies in a mouse model, it is proposed that mammalian embryos, including human, express PPARδ. The expression of PPARδ ensures orderly development of preimplantation embryos, and its activation by synthetic ligand enhances embryo hatching in vitro.

Materials and Methods.

Source of reagents and institutional approval. Unless specified otherwise, all reagents were purchased from Sigma-Aldrich Co. (St. Louis, Mo., USA). The research protocol was approved by the Animal Welfare Committee of the University of Texas Health Science Center at Houston. The care and the manipulation of mice were consistent with the Guide for the Care and Use of Laboratory Animals published by the U.S. National Institute for Health (NIH publication No. 85-23, revised 1996).

Harvest and culture of mouse embryos. Mice were obtained from the following sources: C3H, 129S1/SvImJ and C57BL6/J, the Jackson laboratory (Bar Harbor, Me., USA); ICR and C57BL6/Nhd, Harlan (Indianapolis, Ind., USA); PPARδ−/−, a gift from Dr. R. Evans (the Salk Institute, La Jolla, Calif.). The wild type (WT) counter parts of PPARδ−/− were bred by mating 129S1/SvImJ and the offspring of C57BL6/J×129S1/SvImJ. Mice were kept in temperature and humidity controlled environment (07:00 light on, 19:00 light off) with free access to food and water. The mouse embryos were harvested and cultured as described previously (Huang et al., 2003). Briefly, three-week old female mice were superovulated with intra-peritoneal injection of PMSG (5 IU) followed by hCG (5 IU) 42-46 hrs later. After hCG injection (at 15:00), each female mouse was caged with one male mouse with proven fertility. Unless specified otherwise, embryos (at two-cell stage) were harvested 44-48 hrs later and cultured (17-20 per group) at 37° C. under 5% $CO_2$ in 4-well plates (Nalge Nunc International, Naperville, Ill., USA) containing 600 ul protein-free media. The HTF media (Sage Biopharma, Bedminster, N.J., USA) was used during the first 48 hrs; the αMEM (Irvine Scientific), with Earle's Salts and 2 mM glutamine, was used during the second 48 hrs. After 96 hrs of culture, each embryo was examined for the presence of zona pellucida. Those completely free of the zona pellucida were counted as having completely hatched. The rate of complete hatching was calculated by dividing the number of completely hatched embryos by the number of total embryos. Complete embryo hatching was used as an end point because it is a clear cut endpoint and correlates with the likelihood of implantation and viable pregnancy (Huang et al., 2003; Huang et al., 2004b). The concentration of the vehicle (DMSO) was less than 1:10,000; control embryos received the same concentration of DMSO.

Comparing the development of PPARδ−/− and WT embryos in vivo. The progression of PPARδ−/− and WT embryos in vivo was compared as follows. Embryos were obtained from plugged mice 70 and 96 hrs after hCG injection. These time points were chosen because at 70 hrs after hCG injection, the majority of WT embryos develop into eight-cell or morula stage embryos, and, at 96 hrs after hCG injection, the majority of WT embryos advanced to blastocysts. The developmental stages of embryos obtained at 70 hrs after hCG injection were compared based on embryonic cell number, because a compacted eight-cell embryo and a morula-staged embryo cannot be differentiated reliably based on their morphology under phase contrast microscope. The developmental stages of embryos obtained 96 hrs after hCG injection were determined based on morphology under phase contrast microscope. The embryonic cell number was determined based on nuclear staining with 4'-6-diamidino-2-phenylindole (DAPI), a DNA-binding fluorescence dye, followed by examination with an immunofluorescence microscope under a UV filter (AxioPlan 2, Carl Zeiss, Germany).

5-Bromo-2'-deoxy-uridine (BrdU) uptake and the proliferation index. The proliferation of embryonic cells was determined based on their abilities to incorporate BrdU. The assay was performed using a commercial kit (BrdU Labeling and Detection Kit I, Roche Applied Science, Indianapolis, Ind.) according to manufacturer's protocols with some optimizations. One of the changes was the duration of incubation. Preliminary experiments showed the optimal incubation time to differentiate the proportions of cells in the S-phase between PPARδ−/− and WT embryos was 10 mins. For the comparison between control and L165,041 treated embryos, the optimal time was 6 minutes. The modified procedure is as follows. Immediately after harvest, the embryos were incubated in 100 μl pre-equilibrated HTF medium containing 10 μM BrdU for 10 min at 37° C. under 5% CO2. Following the incubation, the embryos were fixed in ice-cold glycine (50 mM) in 70% ethanol (pH2.0) at −20° C. for 30 mins. Following rehydration/blocking in phosphate buffered saline (PBS) containing 1% BSA, the embryos were incubated with diluted anti-BrdU mouse monoclonal antibody (1:2) in the incubation buffer containing 1% BSA and followed by another incubation with a diluted FITC-conjugated anti-rabbit IgG antibody (1:4) in PBS containing 1% BSA. Both incubations were at 37° C. and lasted for 30 mins; the embryos were washed in 200 μl PBS containing 1% BSA after each incubation. After a final incubation in DAPI (5 μg /ml) for 90 mins at 25° C., the embryos were mounted in 0.1 M Tris HCl (pH 8.5) containing 16.6% Elvanol® 50-42 (DuPont Wilmington, Del., USA) and 2.5% 1,4-diazabicyclo-(2.2.2)-octane. Cells that were in S-phase and, therefore, incorporated BrdU were identified under a FITC filter. Total cell number was determined based on DAPI nuclear staining under a UV filter (AxioPlan 2, Carl Zeiss, Germany). The proliferation index (percent of cells in S-phase) was determined by dividing the number of BrdU-positive cells by the number of total cells then multiplies by 100%.

Terminal deoxynucleotidyl transferase mediated dUTP Nick End Labeling (TUNEL) and dead cell index. The embryonic cells that undergo programmed cell death were identified by TUNEL assay using a commercial kit (In Situ Cell Death Detection Kit, Roche Applied Science) with some modifications. At each time point indicated, embryos were collected after culture or harvested from mice and fixed in 4° C. PBS containing 4% buffered paraformaldehyde for 30 min. Prior to TUNEL, the embryos were incubated at 37° C. with 5% triton in PBS for 20 mins. The manufacturer's protocol was modified. Up to 20 blastocysts were incubated at 37° C. in 20 uL of TUNEL reaction solution (2 uL of TUNEL enzyme and 18 uL of 1:4 diluted labeling solution) in a humidified chamber for 60 mins. The embryos were then incubated in DAPI (30 ug/mL) for 5 mins at 37° C. before mounted in 16.6% Elvanol® 50-42 (Dupont, Wilmington, Del., USA) in 0.1 M Tris HCl pH 8.5. The apoptotic cells and the total cells were visualized using a fluorescence microscope (AxioPlan 2, Carl Zeiss, Germany) with FITC and UV filters, respectively. DNAse-treated embryos were used as positive controls. The dead cell index (percent of cells that were TUNEL positive) was determined by dividing the number of TUNEL-positive cells by the number of total cells then multiplies by 100%.

RNA extraction, RT/PCR and restriction enzyme digestion analysis. Total RNA was extracted from 20 blastocysts using a commercial kit (RNeasy, Qiagen, Chatsworth, Calif., USA) and used for RT/PCR. The primers were selected based on mouse PPARδ sequence from the gene bank (NM_011145). A BLAST analysis showed there was no published mouse sequence that shared homology with the sequence of the 334 bp amplicon. The RT was carried out at 42° C. for 30 mins using a synthetic primer sequence 5' TTCTAGAGCCCGCAGAATGG (Sequence ID No. 1) based on the nucleotide sequence from exon 6. The upstream 5' GCCAAGAACATCCCCAACTTC (Sequence ID No. 2), and downstream 5' CCTGGATGGCTTCTACCTGG (Sequence ID No. 3), primers were from exons 5 and 6, respectively. The PCR reaction consisted of 45 cycles of 94° C. for 15 sec, 60° C. for 1 min and 72° C. for 1 min and concluded with a 7-min extension at 72° C. The amplicon with the expected molecular weight (~330 base pair) was eluted (QIAEX II Gel Extraction Kit) and digested with the restriction enzyme SST1 (Invitrogen, Carlsbad, Calif.). The PCR products and the digested DNA (expected to yield two fragments: 95 and 239 bp) were separated using a 2% and 3% agarose gel, respectively, and visualized with UV light.

Western blot analysis. Western blot analysis was performed as described previously (Huang et al., 2002) with some modifications. Affinity purified, polyclonal antibody against a synthetic peptide based on mouse PPARδ protein (MEQPQEETPEAREE, (i.e. the synthetic sequence for antibody production, Sequence ID No. 4 (Met Glu Gln Pro Gln Glu Glu Thr Pro Glu Ala Arq Glu Glu) Abcam Inc., Cambridge, Mass., USA) was used. Briefly, the proteins in the cell lysate were electrophoresed on a 10% acrylamide gel and transferred to a nitrocellulose membrane (Schleicher & Schuell, Inc., Keene, N.H., USA). The PPARδ protein bound by the antibody was visualized using enhanced chemi-fluorescence (Amersham Biosciences, Piscataway, N.J., USA), whose signals were detected by a STORM 860 laser scanner (Amersham Biosciences). Total cell lysate from mouse liver was used as a positive control.

The cell lysate of blastocysts was prepared as follows. Sixty mouse blastocysts in 2 μL of media were transferred to 1.5 ml Eppendorf tubes containing 30 μL of lysis buffer (150 mM NaCl, 1% NP-40, 0.25% Sodium deoxycholate, 1 mM sodium orthovanadate, 1 mM EGTA and 1 mM sodium fluoride), and protease inhibitors (1 mM 4-(2-aminoethyl) benzene sulfonyl fluoride hydrochloride, 0.8 μM aprotinin, 50 μM betastatin, 15 μM E-64, 20 μM leupeptin hemisulfate, 10 μM pepstatin A, Calbiochem-Novabiochem Corp., San Diego, Calif., USA). The mixture was vortexed for 5 secs, centrifuged for 10 secs and stirred on ice for another 30 mins. After two bursts of sonication (Sonifier 250, Branson Co. Danbury, Conn., USA), one sec each, the lysate was mixed with 4× protein loading dye. The supernatant of the mixture was used for Western blot analysis.

Immunohistochemistry. The same antibody used in the Western blot analysis was used to localize PPARδ in the embryos. The immunohistochemistry was performed as described previously (Huang et al., 2003). Briefly, the embryos (ICR) were fixed in ice-cold PBS containing 4% buffered paraformaldehyde for 30 mins. After permeabilization with 1% triton in PBS for 20 mins, the embryos were incubated at 37° C. with anti-PPARδ antibody (32 μg/mL) in PBS containing 5% milk for 30 mins. Embryos were then incubated at 37° C. in 2.5 μg/mL goat anti-rabbit IgG antibody conjugated with FITC (Molecular Probes, Portland, Oreg.) for 30 mins. Embryos were washed four times in PBS, five minutes each, between the incubations. After a final incubation with DAPI (30 ug/mg) for 5 mins at 37° C., the embryos were mounted as described above (in the TUNEL section) and examined under FITC and UV filters using a fluorescence microscope (AxioPlan 2, Carl Zeiss, Germany). Unfertilized eggs and embryos from various developmental stages (from one-cell embryos to blastocyst-staged embryos) were examined. PPARδ−/− blastocysts were used as negative controls.

Data Analysis

Prism® Version 3.0 (GraphPad Software Inc. San Diego, Calif.), with the Hill slope set at 1.0, was used to estimate the ED50 of L-165041. Chi-square and Student's t-tests were used where appropriate (InStat® Version 3.05, GraphPad Software Inc.). A $p<0.05$ was considered statistically significant.

Results—Section I.

Figure 1B:
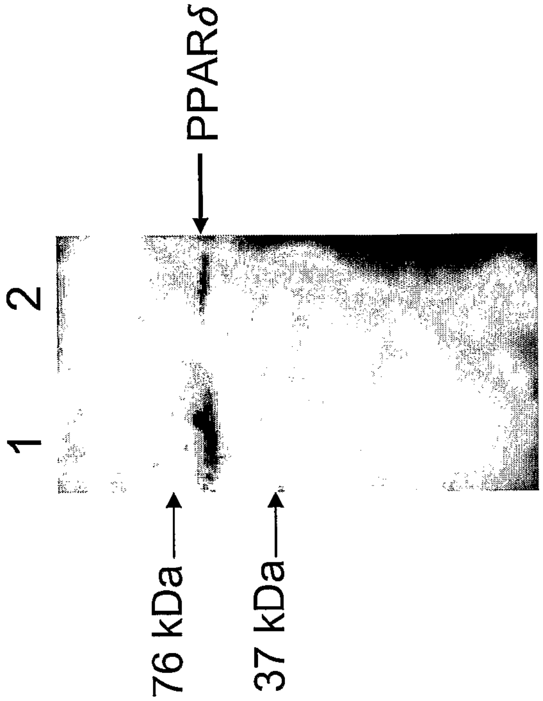

Preimplantation mouse embryos express PPARδ. RT/PCR and Western blot analysis were first performed on blastocysts (C3B6F1) to determine the expression of PPARδ. The primers used for the PCR were from exons 5 and 6, respectively; the expected size of the amplicon was 334 bp. Analysis of PCR products by agarose gel electrophoresis revealed two amplicons: one has the expected molecular weight (~330 bp), the other has a lower molecular weight (~250 bp) (FIG. 1*a*). The 330 bp amplicon was eluted from the gel and digested with a restriction enzyme (SST1). Analysis of the digested products by agarose gel electrophoresis revealed two fragments of expected sizes (~95 and ~240 bp) as predicted by the cDNA sequence of PPARδ (FIG. 1*b*). Western blot analysis on total cell lysate of blastocysts revealed a single band corresponding to PPARδ protein from the liver (FIG. 1*c*).

Figure 2:
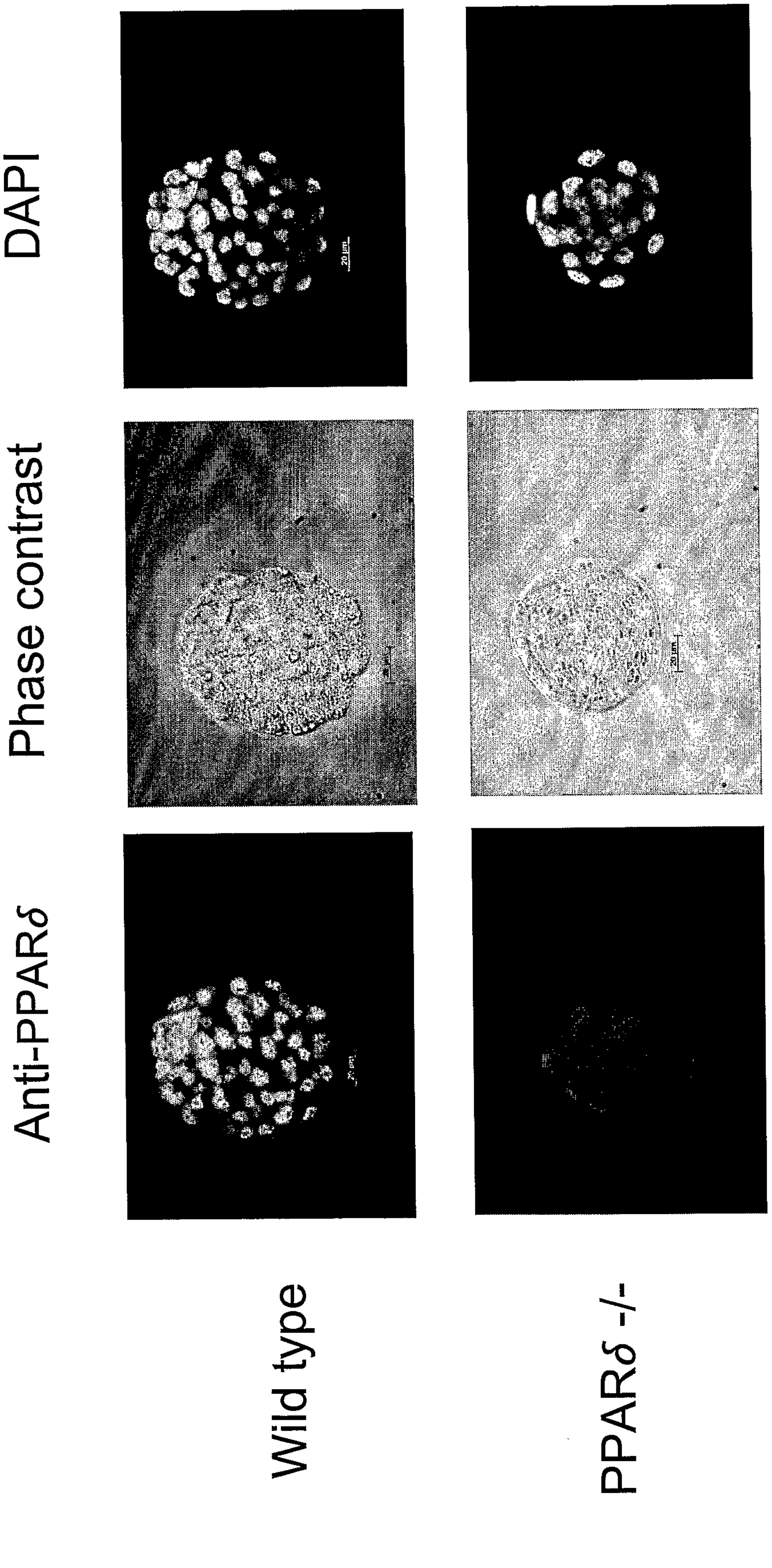
FIG. 2. Peroxisome proliferator activated receptor δ (PPARδ) protein is localized to the nuclei of embryonic cells. The same antibody used for Western blot analysis was used for immunohistochemical localization of PPARδ in outbred strain embryos (ICR). Embryos from various developmental stages and unfertilized eggs were examined. The immunostaining was detected in embryos at eight-cell stage and onward. One representative blastocyst is shown: both inner cell mass and trophoectoderm showed PPARδ staining. The PPARδ staining has a granular pattern and mirrors that of nuclear staining by 4'-6-diamidino-2-phenylindole (DAPI), a DNA binding dye.

PPARδ protein is detectable in eight-cell-staged and onward embryos. The same antibody used in the Western blot analysis was used to localize PPARδ protein in preimplantation embryos. Immunohistochemistry was performed on unfertilized eggs and embryos (ICR, an outbred strain) from various developmental stages. The results show the staining of PPARδ was localized in the nuclei of embryonic cells. It had a granular pattern that mirrored the nuclear staining by the DNA binding dye DAPI. PPARδ first became detectable in eight-cell embryos (not shown). In the blastocysts, both inner cell mass and trophectoderm showed PAPRδ staining (FIG. 2). As expected, PPARδ−/− blastocysts showed no staining.

Figure 3B:
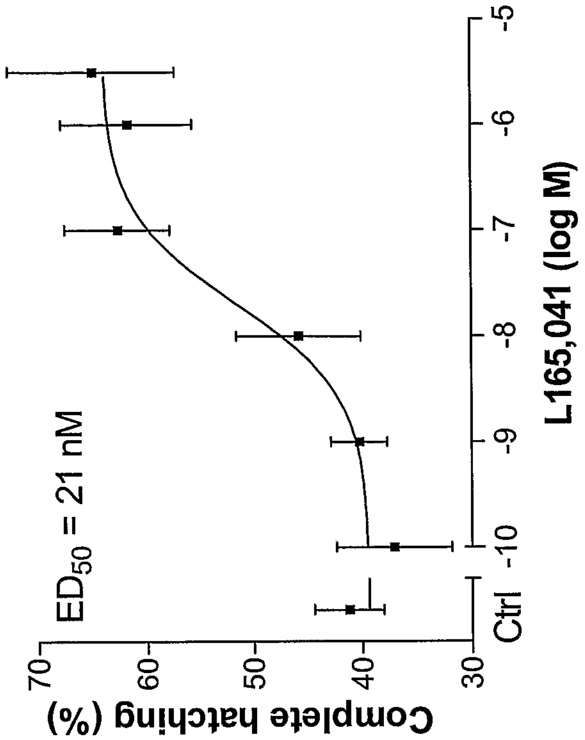
FIG. 3. Specific ligand for peroxisome proliferator activated receptor δ (PPARδ) enhanced mouse embryo hatching in a concentration dependent manner. (a) Two-cell embryos (C3B6F1) were harvested and cultured in the presence of DMSO (vehicle, 1:10,000) or 1 μM of synthetic PPAR ligand: WY14,643 (PPARα), L165,041 (PPARδ) and ciglitazone (PPARγ). Ninety-six hours later, the rates of complete hatching were compared. L165,041, a specific ligand for PPARδ, enhanced complete embryo hatching ($p<0.0001$, X2=24.6 among all groups; $p=0.0097$, Fischer exact test L165,041 versus control group; relative risk=1.9; 95% confidence interval: 1.08-3.36). Numbers in the parentheses denote the number of completely hatched embryos over total embryos. (b) Two-cell embryos (C3B6F1) were cultured in medium supplemented with different concentrations of L165,041 for 96 hrs. The rates of complete hatching were calculated (details see text). The figure depicts the mean±SD of complete hatching (%) based on three to six independent experiments each containing 15-20 embryos. The estimated ED50 was 21 nM. (There were six experiments for 1 μM, three experiments each for 0 and 3 μM, and four experiments each for other concentrations.)
Figure 3A:
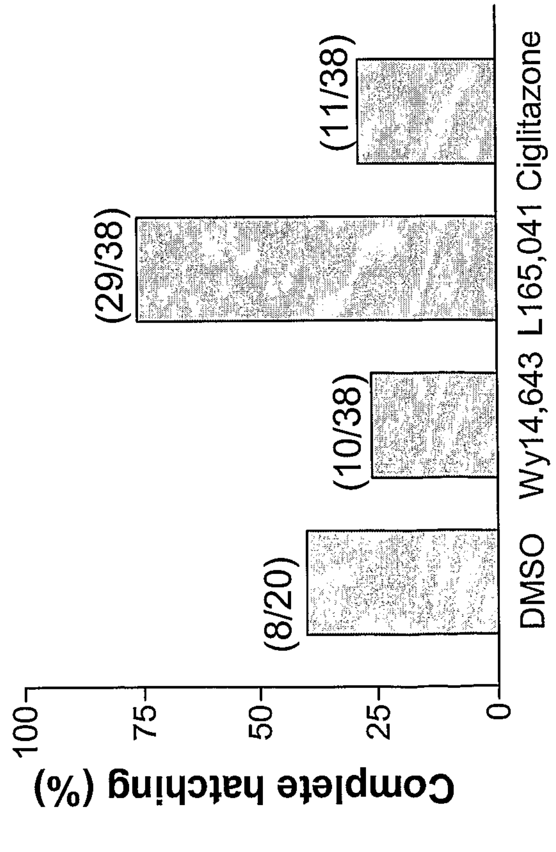

Synthetic PPARδ ligand selectively enhances mouse embryos hatching. To confirm the biological function of PPARδ, the response of embryos to three isotype-specific synthetic PPAR ligands was determined. Two-cell embryos (C3B6F1) were cultured in media supplemented with each ligand for 96 hrs and complete embryo hatching was used as the endpoint. Of the three synthetic PPAR ligands, only L165,041, which interacts specifically with PPARδ, enhanced complete embryo hatching (FIG. 3*a*). L165,041 is 4-[3-(4-Acetyl-3-hydroxy-2-propylphenoxy)propoxy]phenoxy-acetic acid. The addition of L165,041 enhanced embryo hatching in a concentration dependent manner; the ED50 was estimated to be 21 nM (FIG. 3*b*). These results suggest that the PPARδ in preimplantation embryos was functional and that its activation enhanced embryo hatching.

Figure 4:
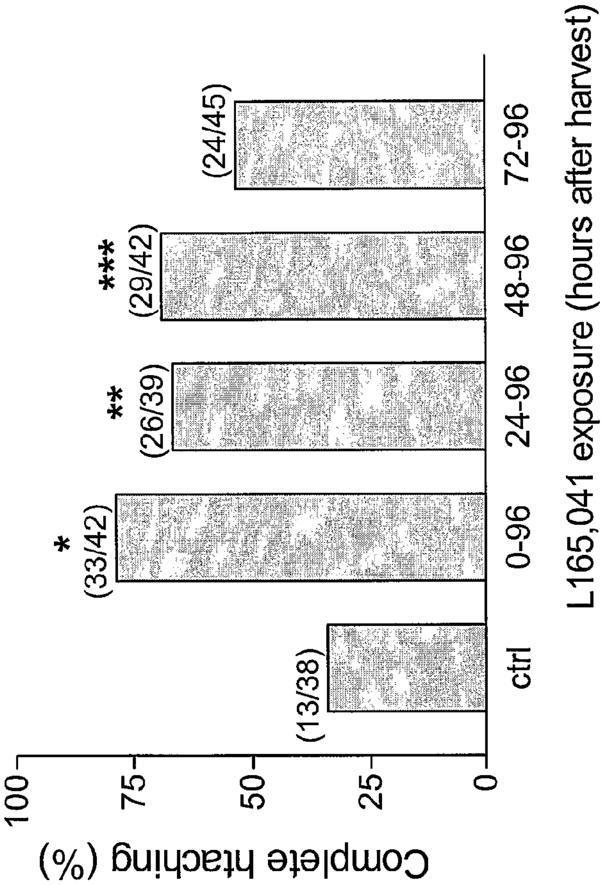
FIG. 4 Morula-staged and onward embryos are responsive to synthetic peroxisome proliferator activated receptor δ (PPARδ). Two-cell embryos (mixed C57BL6N and C3H background) were cultured for 96 hrs in media supplemented with 1 μM L165,041 during the indicated period. The table below shows the developmental stages the embryos went through during the period. Compared with control embryos, embryos exposed to L165,041 during 0-96, 24-96 and 48-96 hrs after harvest had significantly higher rates of complete hatching. These results suggest that 48 hrs after harvest, when the majority of embryos became morula, the embryos became responsive to L165,041. Numbers in the parentheses indicate the numbers of completely hatched embryos versus total embryos. ($p=0.0006$, $X2=19.6$ among the five groups; *$p<0.0001$, $p=0.004$, *$p=0.002$ versus control)

Response to synthetic PPARδ ligand in the preimplantation embryos is developmental stage dependant. Beginning at two-cell stage when the genome become activated, the embryos become progressively responsive to external stimuli. To determine when the embryos become responsive to synthetic PPARδ ligand, the following experiment was performed. Two-cell embryos (C3H and C57BL6Nhd mixed genetic background) were randomly assigned to one of the three groups, where L165,041 was supplemented 24, 48 and 72 hrs after the beginning of culture. At these time points, the majority of them developed into eight-cell-, morula- and blastocyst-staged embryos, respectively. The rates of complete hatching were compared among the groups after 96 hrs of culture. The present results show the groups receiving L165,041 during 24-96 hrs and 48-96 hrs (corresponding to eight-cell stage onward and morula stage onward, respectively) had similar rates of complete hatching as the group receiving L165,041 during 0-96 hrs (FIG. 4). Although embryos receiving L165,041 during 72-96 hrs (corresponding to blastocyst stage onward) appeared to have a higher rate of complete hatching than the control embryos, the difference was not statistically significant ($p=0.08$) (FIG. 4). These results indicate that after 48 hrs of culture, the embryos became responsive to L165,041. Based on the developmental stages of embryos at this time, it can be concluded that embryos became responsive to L165,045 at morular stage and onward. This is consistent with the developmental stage-dependent expression of PPARδ based on immunohistochemistry study.

Figure 5B:
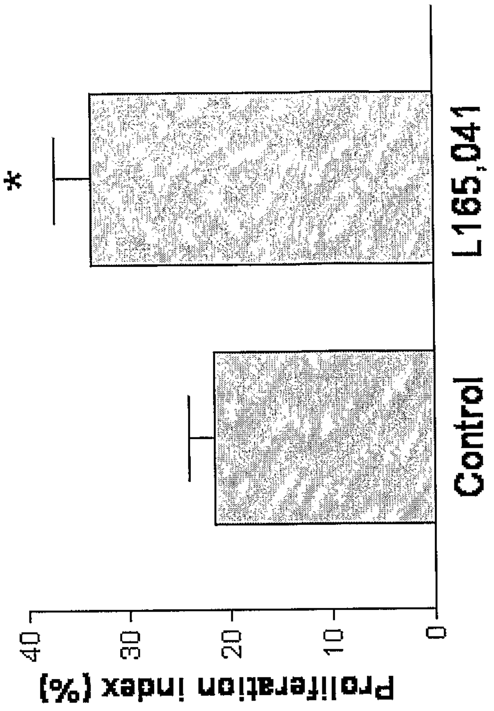
FIG. 5. Synthetic peroxisome proliferator activated receptor δ (PPARδ) ligand decreases apoptosis and increases cell proliferation in preimplantation embryos.
(FIG. 5*a*) Two-cell mouse embryos (C3B6F1) were cultured in media supplemented with L165,041 (0.1 μM, a synthetic PPAR δ ligand) or vehicle (DMSO, 1:10,000) for 72 hrs. All embryos that reached blastocyst stage (typically ~90%) were fixed with paraformaldehyde and underwent TUNEL analysis and nuclear counter staining using 4'-6-diamidino-2-phenylindole. Total and apoptotic cells were determined under a fluorescence microscope with appropriate filters. The results (mean±SD) of 17 control and 19 experimental embryos are depicted. This is the results from one of the three experiments. The other two experiments, using similar number of embryos, yielded similar results. (*$p=0.034$) (FIG. 5*b*) Two-cell embryos (25% C57BL6/J and 75% 129S1/SvImJ) were harvested and cultured for 72 hrs as described above. After incubation with 10 μM 5-bromo-2'-deoxy-uridine (BrdU) for six minutes, the embryos were fixed in acidic ethanol containing glycine (details in text). The incorporated BrdU was detected by immunohistochemistry using specific monoclonal antibody against BrdU. The proliferation index is the percentage of cells incorporating BrdU in an embryo. The results (mean±SD) from 25 control and 31 experimental embryos are presented. The average number of cells per embryo was 63 in both groups. (*$p=0.015$)
Figure 5A:
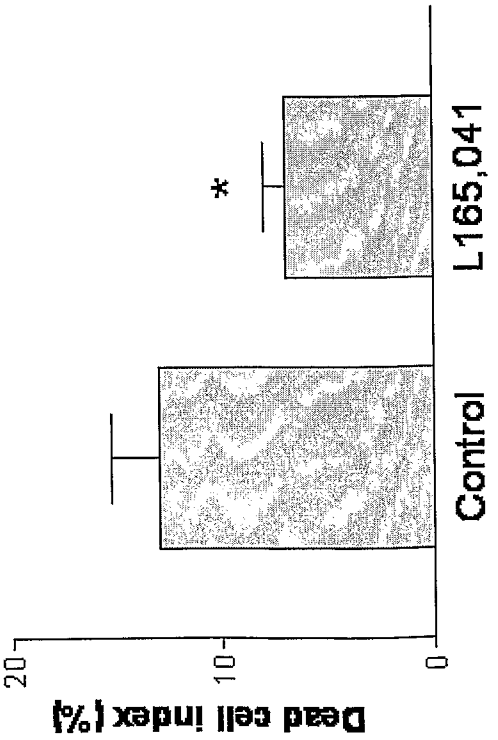

Synthetic PPARδ ligand decreases apoptosis and increases cell proliferation in preimplantation embryos. Previous study indicates that successful embryo hatching in vitro depends on a sufficiently high number of cells (Montag et al., 2000). Initial studies showed that total cell number could be determined reliably in an embryo after 72 hrs of culture, but not after 96 hrs. Therefore, in subsequent studies the rates of apoptosis and proliferation in embryos were compared after 72 hrs of culture. Apoptotic cells and cells in the S-phase were determined using TUNEL assay and BrdU incorporation, respectively; DAPI, a DNA binding dye, was used to determine total embryonic cells. The results show that the number of cells in control and experimental embryos were comparable (about 60 per embryo) after 72 hrs of culture, but L165,041-treated embryos had less dead cells and more cells in the S-phase (FIG. 5). These results suggest that given additional 24 hrs, when the complete embryo hatching is assessed, L165,041-treated embryos are likely to have more live cells.

Figure 6:
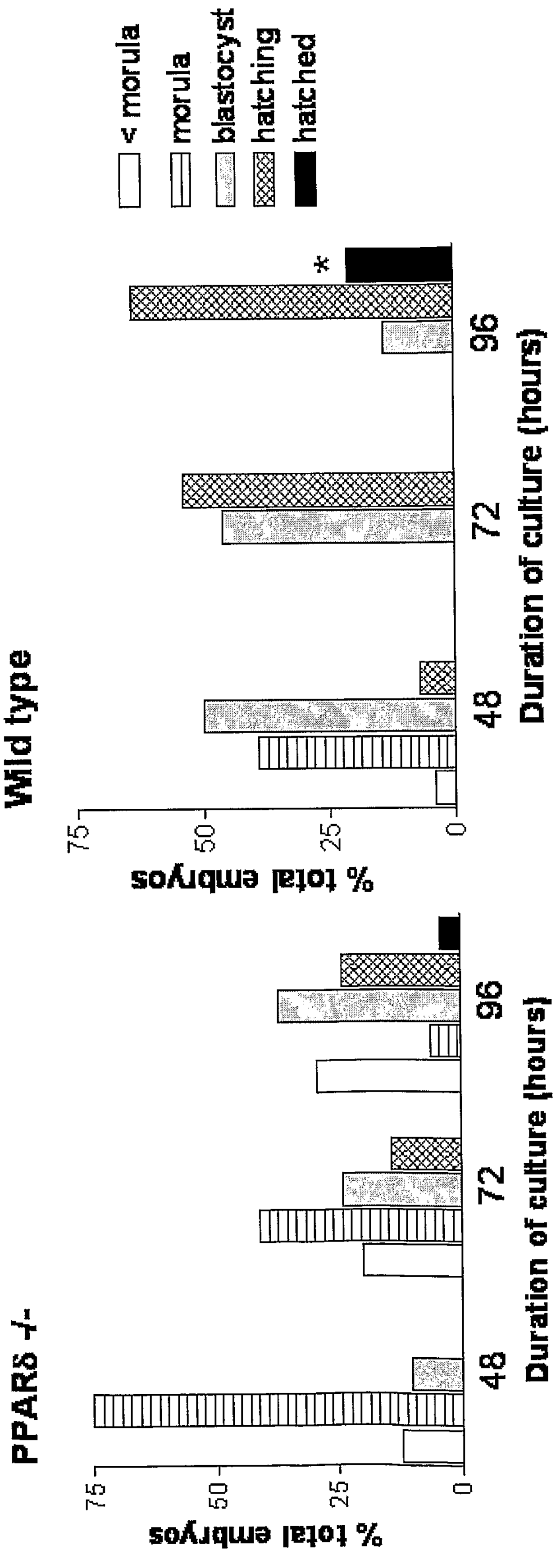
FIG. 6. The ablation of peroxisome proliferator activated receptor δ (PPARδ) delays the orderly progression of preimplantation embryos in vitro. PPARδ−/− and wild type embryos (WT) were harvested 47 hrs after hCG injection and observed in vitro for 96 hrs. The disparity in development became clear after 48 hrs of culture. The figure is based on 151 PPAR δ−/− and 84 WT embryos. The experiment was repeated once using similar number of embryos and the results were similar. (*$p=0.0261$, two-sided Fisher's exact test, relative risk=5.393, 95% confidence interval=1.113 to 26.138)

PPARδ is critical to the orderly progression of preimplantation embryos in vivo and in vitro. To explore the role of PPARδ in the development of preimplantation embryos, the development of PPARδ−/− and WT embryos in vitro and in vivo was compared. For the former, two-cell embryos were cultured and observed for 96 hrs; for the latter, embryos were retrieved 70 and 96 hrs after hCG injection (see Material/Method section for rationale). The results show that PPARδ deficiency hampered embryo development. The difference in development became clear after 48 hrs of culture, when 57% WT embryos became either blastocysts or hatching blastocysts whereas 10% PPARδ−/− embryos advanced to blastocysts. The disparity remained at the end of 96 hrs: 21% of WT embryos and 4% of PPARδ−/− embryos hatched completely (FIG. 6). It is worth mentioning that PPARδ−/− embryos did not "catch up" with the WT embryos even after the duration of culture was extended to 120 hrs: during 96-120 hrs, some embryos remained unchanged whereas others became degenerated (data not shown).

Figure 7A:
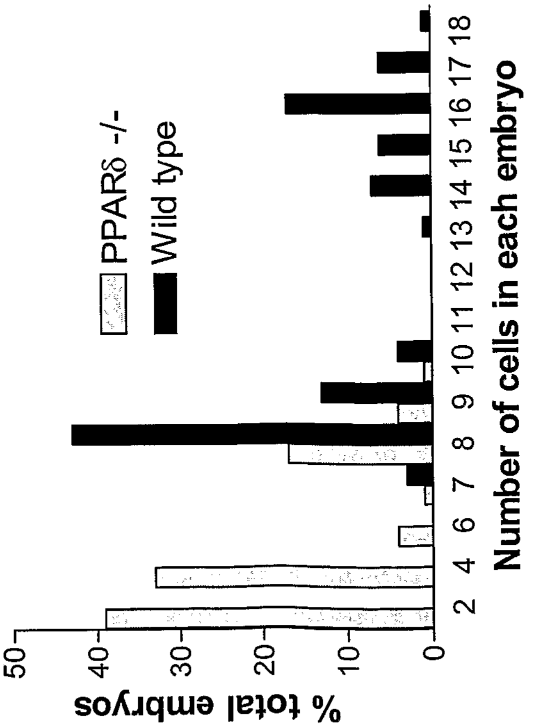
FIG. 7. The ablation of peroxisome proliferator activated receptor δ (PPARδ) delays the orderly progression of preimplantation embryos in vivo. PPARδ−/− and wild type (WT) embryos were obtained 70 and 96 hrs after hCG injection. The developmental stages of the embryos were determined based on the morphology under an inverted microscope; the number of cells in each embryo was determined by nuclear staining with 4'-6-diamidino-2-phenylindole (DAPI), a DNA-binding fluorescence dye. At 70 hrs after hCG injection, (a) the majority of the PPARδ−/− and WT embryos were four- and eight-cell embryos respectively, and (b) as expected, WT embryos have significantly more cells than PPARδ−/− embryos (*$p<0.0001$). At 96 hrs after hCG injection, (c) significantly more WT than PPARδ−/− embryos were at blastocyst stage (*$p<0.0001$, relative risk 2.6, 95% confidence interval 1.8-3.6), and (d) WT embryos have significantly more cells than PPARδ−/− embryos (*$p=0.002$). The results in (a) and (b) were based on 76 PPARδ−/− embryos and 72 WT embryos; those in (c) were based on 155 each of PPARδ−/− and WT embryos; those in (d) were based on nine PPARδ−/− embryos and 18 WT embryos.
Figure 7B:
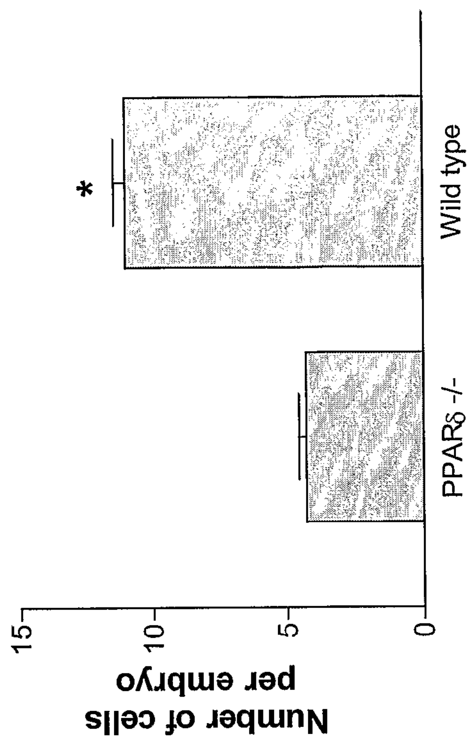
Figure 7C:
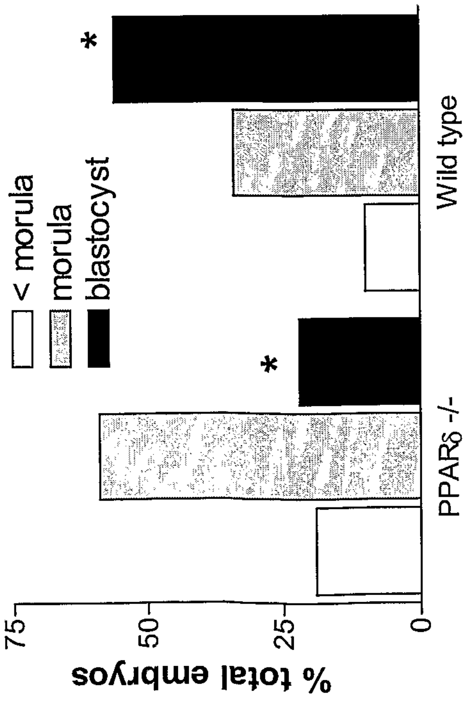
Figure 7D:
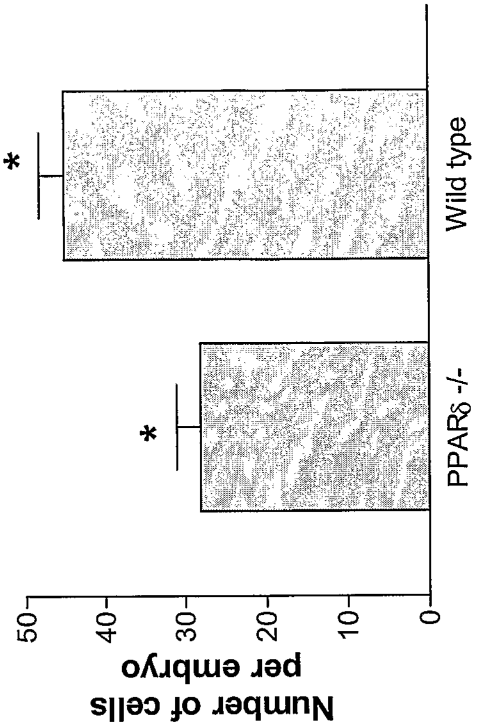

The contrast in in-vitro development between PPARδ−/− and WT embryos also appeared in embryos harvested 70 and 96 hrs after hCG injection. At 70 hrs after hCG injection, the majority of WT embryos became eight-cell embryos, whereas the majority of PPARδ−/− embryos were two- or four-cell embryos (FIG. 7*a*). Similarly, at 96 hrs after hCG injection, 56% of WT embryos and 22% of PPARδ−/− embryos advanced to blastocysts (FIG. 7*c*). As expected, WT embryos had significantly more cells than PPARδ−/− embryos (FIGS. 7*b* and 7*d*). These results suggest that PPARδ is critical to the orderly progression of preimplantation embryos.

Figure 8:
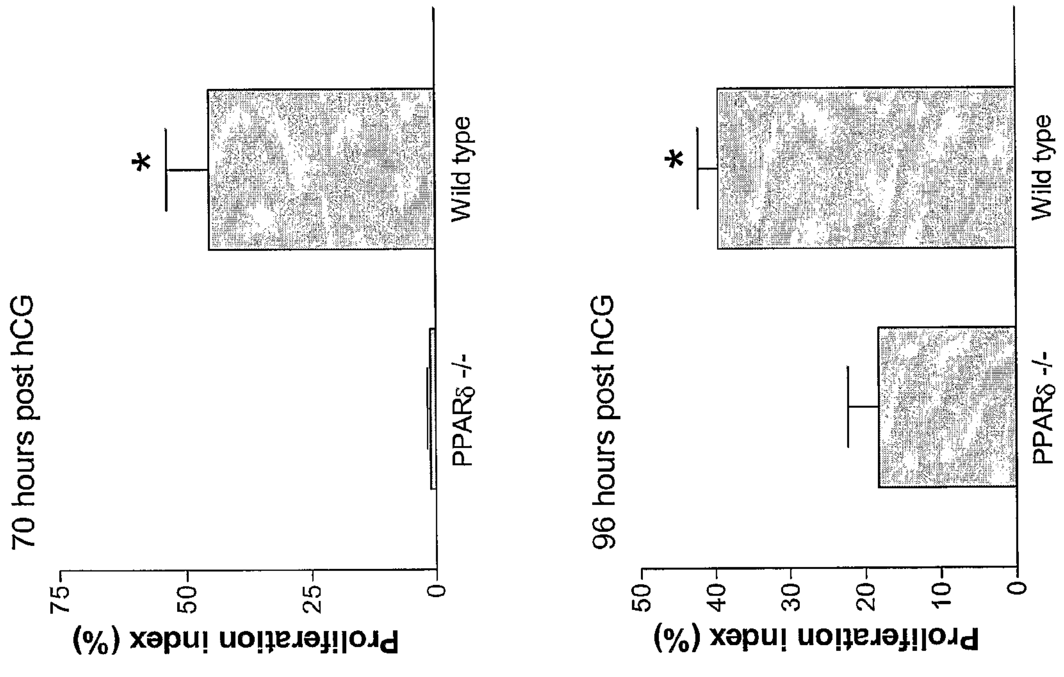
FIG. 8. The ablation of peroxisome proliferator activated receptor 6 (PPARδ) is associated with decreased embryonic cell proliferation. PPARδ−/− and WT embryos were obtained 70 and 96 hrs after hCG injection and incubated in medium containing 5-bromo-2'-deoxy-uridine (BrdU, 10 μM) for 10 min. The embryos were fixed in ice-cold glycine (50 mM) in 70% ethanol (pH2.0), stained with anti-BrdU mouse monoclonal antibody and FITC-conjugated anti-rabbit IgG antibody (details see text). The nuclei of cells were stained by 4'-6-diamidino-2-phenylindole (DAPI, 5 μg/ml), a DNA binding dye. Cells that were in S-phase and, therefore, incorporated BrdU were identified under a FITC filter. Total cell number was determined based on DAPI nuclear staining under a UV filter. The proliferation index (percent of cells in S-phase) was determined by dividing the number of BrdU-positive cells by the number of total cells then multiplies by 100%. At (a) 70 hrs and (b) 96 hrs after hCG injection, WT embryos had significantly higher proliferation index than PPARδ−/− embryos. Twelve embryos each were used for (a); 33 WT embryos and 30 PPARδ−/− embryos were used in (b). (*$p<0.0001$)

Ablation of PPARδ is associated with decreased embryonic cell proliferation but not increased apoptosis. To determine the extent to which different rate of cell proliferation contributed to the developmental disparity in PPARδ−/− and WT embryos, BrdU labeling in embryos harvested 70 and 96 hrs after hCG injection was performed. The results show that more WT embryos incorporated BrdU than PPAR −/− embryos and that WT embryos had higher proliferation indices. At 70 hrs post hCG injection, 92% of the WT embryos and 4% of the PPARδ−/− embryos incorporated BrdU. The proliferation indices of WT and PPARδ−/− embryos were 45% and 1%, respectively (FIG. 8*a*). Similarly, at 96 hrs post hCG injection, 100% WT embryos incorporated BrdU, compared with 57% of the PPARδ−/− embryos. The proliferation indices of WT and PPARδ−/− embryos were 40% and 18%, respectively (FIG. 8*b*). To determine the extent to which apoptosis led to the developmental delay in PPARδ−/− embryos, embryos were obtained 96 hrs after hCG injection, the TUNEL assay was performed, and then dead cell indices were compared. The results showed 28 of 61 (54%) PPARδ−/− embryos and one of the 58 (2%) WT embryos examined were developmentally arrested; they contained 15 or less cells per embryo. Three of these embryos stained positive for TUNEL: one TUNEL positive cell each in two embryos, two TUNEL positive cells in the third embryo. The dead cell indices in embryos containing 16 or more cells were comparable: 2.2±3.5% versus 2.9±3.9% (mean SD of 33 PPARδ−/− embryos and 58 WT embryos, p=0.33). These results suggest that ablation of PPARδ in preimplantation embryos is associated with decreased cell proliferation but not increased apoptosis.

Discussion—Section I.

It is shown here for the first time that preimplantation mouse embryos express PPARδ. Its activation by synthetic PPARδ ligand enhanced embryo hatching and reduced apoptosis; its ablation by genetic targeting led to an irreversible delay in embryo development due to decreased cell proliferation.

The present findings corroborate an earlier report regarding the expression and the proposed biological functions of PPARδ. In E8.5 day rat embryos (the earliest developmental stage examined thus far), ubiquitous PPARδ message (but not PPARα or PPARγ messages) was revealed by in-situ hybridization (Braissant et al., 1998). Based on those findings, it was proposed that PPARδ may participate in more basic cellular functions such as membrane lipid turnover or cell cycle progression. The present results go beyond the earlier reports, however, and show that lack of PPARδ expression in preimplantation embryos is associated with decreased embryonic cell proliferation and irreversible developmental delay.

Although PPARδ has been implicated in cell proliferation, its exact role is controversial. Whereas over-expression of PPARδ in cultured vascular smooth muscle cells promotes the proliferation of post-confluent cells (Julan et al., 2005), PPARδ+/−mutant mice respond more profoundly to proliferation stimuli than the wild type mice (Michalik et al., 2001; Tan et al., 2001). An increase of cyclin A and Cdk2 and a decrease of p57kip2 (a Cdk2 inhibitory protein) have been proposed to be the mechanisms for the former; it is not clear what causes the latter. In preimplantation mouse embryos, the ablation of PPARδ is associated with a significant decrease in cell proliferation and the activation of PPARδ is associated with a significant increase in cell proliferation. PPARδ activation is likely to enable embryonic cells to overcome G1-restriction point and facilitate their entry into the S-phase. The present experimental results showing that synthetic PPARδ ligand increases cell proliferation in WT embryos are consistent with the growth promoting properties of PPARδ in the former report.

Previous studies regarding PPARδ activation and decreased apoptosis are more consistent. The anti-apoptosis properties of PPARδ has been proposed to facilitate wound healing of skin (Michalik et al., 2001; Wahli 2002) and increase the resistance to hypertonic stress in kidney cells (Hao et al., 2002). It may also play a central role in the tumorigenesis of colorectal cancer (Gupta et al., 2000; Cutler et al., 2003). The present experimental results showing that synthetic PPARδ ligand reduces apoptosis in WT embryos are consistent with the previous reports of anti-apoptosis properties of PPARδ.

The molecular mechanisms involving increased cell proliferation and decreased apoptosis in L165,041-treated embryos remain to be determined. Without wishing to be limited to a particular theory, it is suggested that the mechanisms may perhaps involve ligand dependent transcriptional activation and co-repressor BCL-6 mediated transcriptional repression. Liganded PPARδ reportedly upregulates the expression of 14-3-3, which in turn upregulates the expression of anti-apoptotic members of the Bcl2 family (Liou et al., 2004). Recent evidence indicates that apo-PPARδ sequesters co-repressor BCL-6 and that, upon binding by the PPARδ ligand, apo-PPARδ releases BCL-6, which is now free to repress the transcription of other genes (Shi et al., 2002). Genes known to be repressed by BCL-6 include cell cycle inhibitor such as p27kip1 (Shaffer et al., 2000; Kusam et al., 2004). This transcriptional activation/repression coupling may also involve other cell cycle regulators. For example, increased cyclin A and Cdk2 and decreased p57kip2 (a Cdk2 inhibitory protein) expression reportedly lead to the proliferation of post-confluent cells over-expressing PPARδ (Julan et al., 2005).

Contrary to what was observed in PPARδ ligand-treated WT embryos (i.e., reduced apoptosis but comparable total cell number), PPARδ−/− embryos did not have more apoptosis than WT embryos. PPARδ−/− embryos had markedly decreased cell proliferation but no appreciable increase in apoptosis. There may be several possible reasons for this observation. Firstly, at 96 hrs post hCG injection, 54% of the PPARδ−/− embryos (compared with 2% of WT embryos) had less than 16 cells, a cell number that should have been achieved at 72 hrs after hCG injection. All but three of these severely delayed embryos showed TUNEL staining. Without wishing to be limited to any particular theory, it is suggested that perhaps these severely delayed embryos underwent apoptosis earlier and that the DNA damage may be so severe that they no longer stained positive by TUNEL assay. Secondly, soluble factors from the oviduct may compensate for PPARδ deficiency and maintain a “normal” rate of apoptosis in in vivo embryos. Embryos co-cultured with human oviductal cells are know to have significantly less apoptosis (Xu et al., 2000). Thirdly, it is possible, although not likely, that functions of synthetic PPARδ ligand such as L165,041 may be different from those of natural PPARδ ligands.

These findings provide new insights into the reproductive phenotypes of PPARδ−/− mice. Although PPARδ ablation is frequently lethal, those surviving PPARδ−/− mice are generally healthy and fertile (Barak et al., 2002). One of the reproductive phenotypes of PPARδ−/− mice is small litter size (personal communication with Dr. R. Evans). This has been attributed to abnormal placento-decidual contact leading to mid-gestational death (Barak et al., 2002), i.e., a postimplantation event. The present observations indicate that high attrition of PPARδ−/− embryos during the preimplantation period may be another cause. PPARδ−/− and WT females responded equally well to super-ovulation by PMSG (number of eggs retrieved from 11 PPARδ−/− and seven WT mice were 26.0±17.2 and 33.1±22.7, mean±SD, respectively); PPARδ−/− and WT males impregnate the females with comparable efficiency (the fertilization rates of the above eggs were 93% and 95%, respectively). However, irreversible developmental delay became evident in PPARδ−/− embryos 70 hrs after ovulation was triggered by hCG (FIG. 7*a*). Thus, loss of embryos during the preimplantation is another cause for the small litter of PPARδ−/− mice.

Synthetic PPARδ ligand may have potential application in human IVF. It has been previously reported that iloprost, a PGI2 analog, enhances embryo hatching (Huang et al., 2003) and that iloprost-treated embryos yielded 28% more live births over control embryos when transferred to gestational carriers (Huang et al., 2004b); PCT/US2004/029167 (Huang et al.), the disclosures of which are hereby incorporated herein by reference. Since L165,041 (a synthetic PPARδ ligand) enhances embryo hatching, it is likely that medium supplemented with synthetic PPARδ ligand may also enhance the live birth potentials of embryos and increase IVF success. It is possible that PPARδ and PGI2 may exert additive or even synergistic effects on the embryos. Therefore, supplementing IVF media with both PGI2 analog and synthetic PPARδ ligand may offer even better IVF success than the ligand alone or PGI2 analog alone. The results observed using the above-described mouse model are believed to be predictive, at least to some extent, of results that will be obtained with other mammalian embryos, including human. Of course, the use of the PPARδ ligand in human IVF requires further safety studies before therapeutic application. It is believed that all PPARδ ligands, including the synthetic compound GW501516 (2-Methyl-4-((4-methyl-2-(4-trifluoromethylphenyl)-1,3-thiazol-5-yl)-methylsulfanyl)phenoxy-acetic acid (Calbiochem, U.S.A.)), have activity, to at least some extent, like that demonstrated with the representative ligand L165,041.

II. Enhancement of Embryo Hatching and Implantation

A series of further studies were carried out to investigate enhancement via the PPARδ pathway of embryo hatching and implantation. Except as noted below, the materials and methods employed were as described above.

Western Blot Analysis (II)

Western blot analysis was performed as described previously (Huang et al., 2004c), using an affinity purified, polyclonal antibody (Abcam Inc., Cambridge, Mass.) against a mouse PPARδ peptide (MEQPQEETPEAREE, Sequence ID No. 4). Twenty-five mouse blastocysts in 2 μl of media were transferred to 1.5 ml Eppendorf tubes containing 30 μl of lysis buffer (150 mM NaCl, 1% NP-40, 0.25% Sodium deoxycholate, 1 mM sodium orthovanadate, 1 mM EGTA and 1 mM sodium fluoride), and protease inhibitors (1 mM 4-(2-aminoethyl) benzene sulfonyl fluoride hydrochloride, 0.8 μM aprotinin, 50 μM betastatin, 15 μM E-64, 20 μM leupeptin hemisulfate, 10 μM pepstatin A, Calbiochem-Novabiochem Corp., San Diego, Calif.). The mixture was vortexed for 5 sec, centrifuged for 10 sec and stirred on ice for another 30 min, followed by two 1-sec bursts of sonication (Branson Co., Danbury, Conn.). After being mixed with 4× protein loading dye, the supernatant was used for Western blot analysis. The lysate was electrophoresed on a 12% gradient acrylamide gel and transferred to a nitrocellulose membrane (Schleicher & Schuell, Inc., Keene, N.H). The PPARδ protein bound by the antibody was visualized using enhanced chemi-fluorescence (GE Healthcare Bio-Sciences Corp., Piscataway, N.J.), whose signals were detected by a STORM 860 laser scanner (GE Healthcare Bio-Sciences Corp). Total cell lysate from mouse testes was used as a positive control. The cell lysate of blastocysts was prepared as follows.

Immunohistochemistry (II)

The immunohistochemistry was performed as described previously (Huang et al., 2004c). In brief, embryos were fixed in ice-cold PBS containing 4% buffered paraformaldehyde for 30 min. After permeabilization with 1% triton X-100 in PBS for 20 min, the embryos were incubated at 37° C. with anti-PPARδ antibody (32 μg/ml) in PBS containing 5% milk for 30 min. The embryos were then incubated at 37° C. in goat anti7 rabbit IgG antibody conjugated with FITC (2.5 μg/ml, Invitrogen) for 30 min. Between incubations, embryos underwent four 5-min washes in PBS. After a final 5-min incubation in Hoechst 33258 (30 μg/ml) at room temperature, the embryos were mounted and examined under FITC and UV filters. Unfertilized eggs and embryos from various developmental stages (from one-cell embryos to blastocyst-staged embryos) were examined.

5-Bromo-2'-deoxy-uridine (BrdU) Uptake (II)

The proliferation of embryonic cells was determined based on their abilities to incorporate BrdU. The assay was performed using BrdU Labeling and Detection Kit I (Roche Applied Science, Indianapolis, Ind.) according to manufacturer's protocols with modifications. In brief, embryos were incubated in 100 μl pre-equilibrated HTF media containing 10 μM BrdU for 6 min at 37° C. under 5% $CO_2$, fixed in ice-cold glycine (50 mM) in 70% ethanol (pH 2.0) at −20° C. for 30 min, and incubated at 37° C. for 30 min with diluted anti-BrdU mouse monoclonal antibody (1:2) buffer containing 1% BSA. Embryos were washed in 200 μl PBS containing 1% BSA and incubated at 37° C. for 30 min with diluted FITC-conjugated anti-rabbit IgG antibody (1:4) in PBS containing 1% BSA. After washing, embryos were treated with Hoechst 33258 (30 μg /ml) for 5 min at 25° C., and mounted in 0.1 M Tris HCl (pH 8.5) containing 16.6% elvanol 50-42 (DuPont, Wilmington, Del.) and 2.5% 1,4-diazabicyclo-(2.2.2)-octane. Cells that incorporated BrdU were identified under a FITC filter (AxioPlan 2, Zeiss, Oberkochen, Germany). Total cell number was determined based on Hoechst 33258 nuclear staining under a UV filter.

Embryo Transfer and Determination of Implantation Rate

Embryo transfer was performed as described previously (Huang et al., 2004b). Briefly, embryos were transferred to gestational carriers (ICR female mice) on day 2.5 of pseudopregnancy under a dissecting microscope (Olympus SZ-PT, Shinjuku-ku, Tokyo, Japan). After anesthesia, each uterine horn was accessed via a 1.5 cm flank incision. With the proximal oviduct held by a pair of forceps, an opening was created at the distal end of the uterine horn on the anti-mesenteric side with a 30 gauge needle. The opening permitted the entry of the transfer pipette which had an inner diameter of 135 μm (MidAtlantic Diagnostics, Inc., Mount Laurel, N.J.). Up to seven embryos in 1.5 μl transfer medium (MEM with 25 mM HEPES and 1% BSA) were transferred to each horn. After each transfer, the contents of the pipette were examined under a stereomicroscope to identify retained embryos. To avoid the mixing of embryos as a result of embryo crossover (Dr. Andreas Zimmer, University of Bonn, Germany, MG118 List, the Jackson Laboratory), each gestational carrier received only one kind of embryo. To maintain consistent transfer techniques, the embryo transfer was performed following the same protocol and by one individual (J-C H). Seventy-two h after embryo transfer, the rates of implantation were determined based on a previously-described method with modifications (Paria et al., 1993). Briefly, 3 min before euthanasia, 0.1 ml of Chicago blue (1%) was injected via the tail vein of the gestational carrier. After the carrier was sacrificed, the uterine horns were opened and the gestation sacs counted. The implantation rate was expressed as percentages of gestation sacs over total embryos transferred. Ninety-seven wild type and fifty-four PPARδ−/− embryos were transferred to seven and four gestational carriers, respectively.

Results—Section II.

Essential Role of PPARδ in Preimplantation Embryo Development in vitro.

Figure 9A:
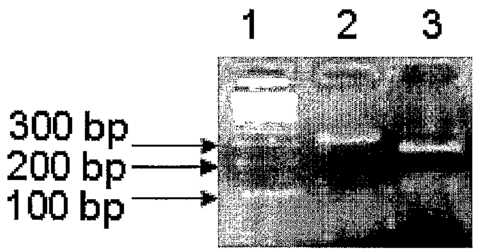
FIG. 9. Preimplantation embryos express PPARδ. (a) Analysis of PPARδ transcripts by RT-PCR. Total RNA was prepared from 20 blastocysts. Lane 1 shows the molecular size markers, lane 2, a 334-bp PPARδ band, and lane 3, confirmation of the 334-bp PPARδ band by SST1 digestion yielding two fragments of expected sizes, 95- and 239-bp, respectively. (b) Western blot analysis of cell lysates from 25 mouse embryos. Total cell lysates of testes (30 μg) were included as a reference; a 60 kd protein was used as a molecular weight marker (lane one). (c) The immunohistochemical staining of PPARδ in a representative blastocyst. The staining pattern suggests the nuclear localization of PPARδ, and is similar to that of Hoechst 33258 (a DNA-binding dye) staining. As expected, PPARδ−/− blastocyst showed no PPARδ staining.
Figure 9B:
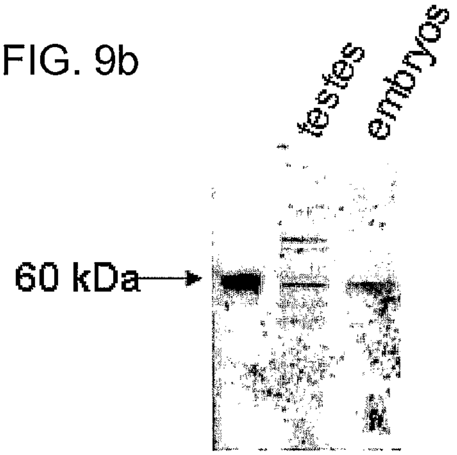
Figure 9C:
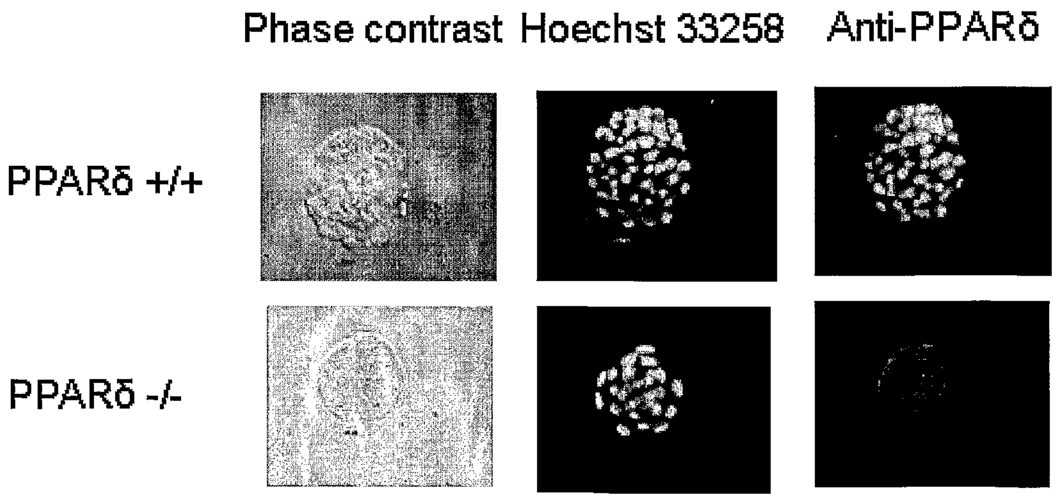
Figure 10:
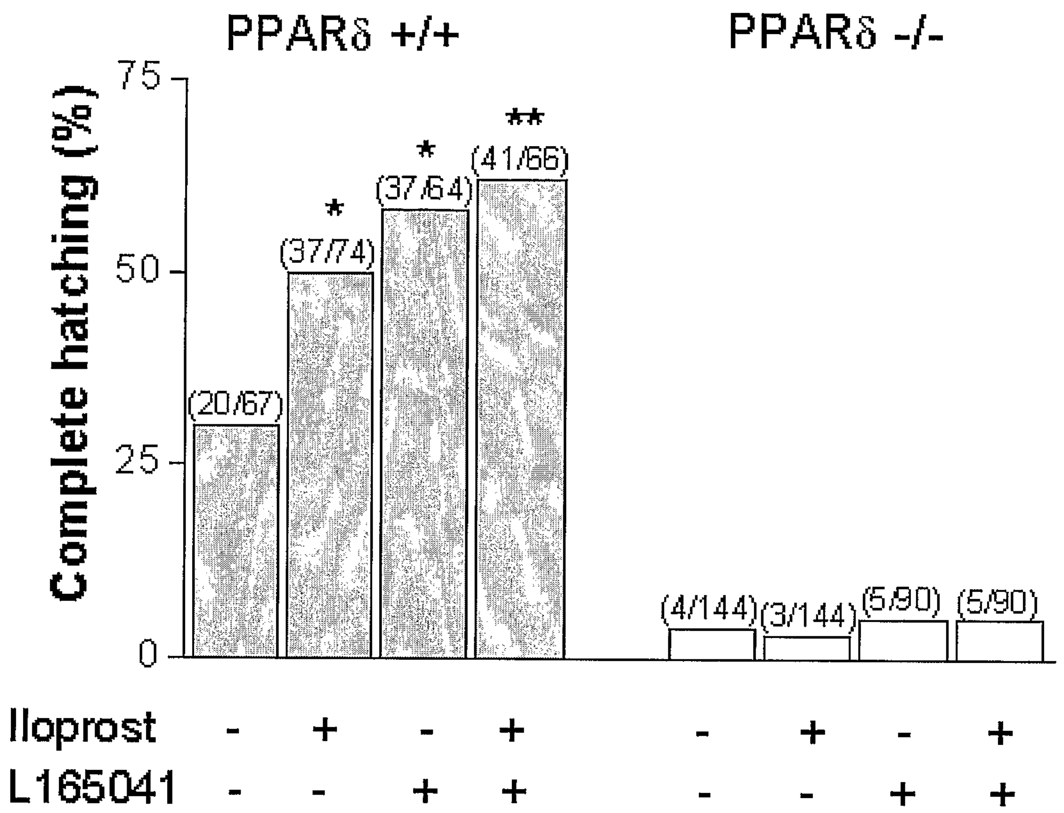
FIG. 10. Effects of iloprost and L-165041 on the hatching of wild type (PPARδ+/+) and PPARδ−/− embryos. Embryos were cultured in the presence or absence of iloprost (0.1 μM) or L-165041 (0.1 μM), beginning at the two-cell stage. After 96 h, the number of completely hatched embryos in each group was compared. Iloprost and L-165041 individually enhanced the hatching of wild type embryos to a similar extent. The combination of iloprost and L-165041 had no additional effects. On the other hand, PPARδ−/− embryos had significantly lower rates of complete hatching and did not respond to either iloprost or L-165041. The numbers in the parentheses denote the number of completely hatched embryos versus total embryos. * denotes $p<0.05$ and ** denotes $p<0.01$ (versus control embryos, Chi-square test).
Figure 11A:
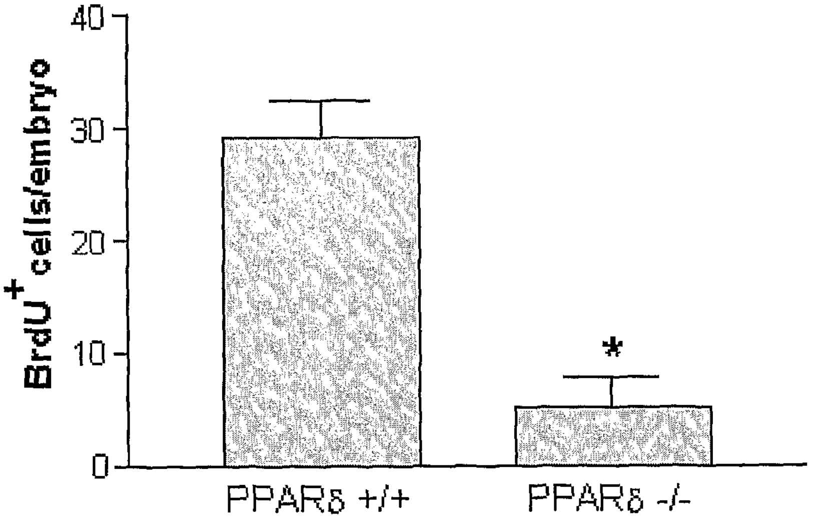
FIG. 11. PPARδ deletion decreases embryonic cell proliferation. Wild type and PPARδ−/− embryos were cultured for 72 h beginning at the two-cell stage. BrdU uptake and cell numbers were determined as described in the method section. WT embryos had more cell proliferation as suggested by significantly more BrdU positive cells per embryo (a). As a result, WT embryos have more cells per embryo (b). The figure depicts the result of one representative experiment using 22 wild type and 20 PPARδ−/− embryos; same results were observed in two other experiments using similar number of embryos. * denotes $p<0.01$.
Figure 11B:
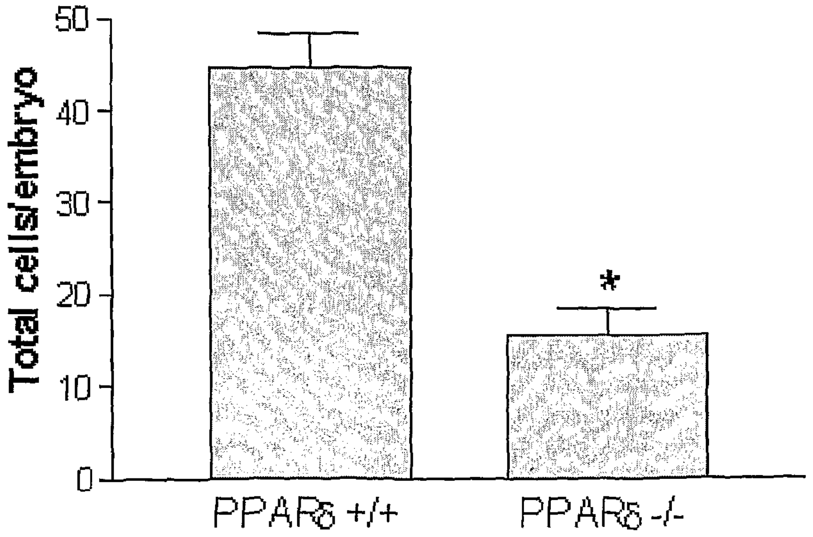

Blastocyst staged embryos expressed PPARδ mRNAs and proteins as determined by RT-PCR and Western blots, respectively (FIGS. 9*a* and 9*b*). PPARδ was detected in eight-cell staged and onward WT embryos but was not detected in PPARδ−/− embryos (FIG. 9*c* upper vs. lower panels). To evaluate the role of PPARδ in embryo development, we compared blastocyst hatching between PPARδ+/+ and PPARδ−/− embryos. Two-cell staged embryos prepared from PPARδ WT and null mice were cultured in vitro for 96 h. Completely hatched embryos were counted. Thirty percent (20/67) of the PPARδ+/+embryos had hatched completely at 96 h compared with 3% (4/144) of PPARδ−/− embryos (FIG. 10). Iloprost (0.1 μM) increased the number of completely hatched embryos to 50% (37/74) in WT but had no effect on PPARδ−/− embryos (3/144). L-165041, a specific PPARδ ligand, increased the proportion of completely hatched embryos to 54%, as compared with 30% in untreated WT embryos. Neither iloprost nor L-165041 affected the hatching of PPARδ−/− embryos. Combined iloprost and L-165041 treatment increased hatched embryos to 52%, an enhancement which is not significantly greater than that of either ligand alone. These results suggest that iloprost and L-165041 act via PPARδ. Experiments were then performed to determine the role of PPARδ in embryo development. Two-cell embryos from WT and PPARδ−/− mice were cultured in media without PPARδ ligands for 96 h. At 48 h, 72 h, and 96 h, blastocysts, morula and earlier-staged embryos (designated <morula) were counted. PPARδ−/− embryos developed significantly more slowly than WT embryos at each time point. At 96 h, 29% of the PPARδ−/− embryos remained at stages earlier than morula and 28% were hatching or hatched, whereas all WT embryos had reached the blastocyst stage and 85% underwent hatching or had completely hatched (Table I). It is worth mentioning that preliminary experiments showed that extending the culture to 120 h did not change the percentages of completely hatched embryos in either group (not shown). Taken together, these data indicate that PPARδ is fundamental to embryo development and hatching in vitro. Embryo hatching is influenced by blastocyst cell numbers (Montag et al., 2000) which cause thinning of zona pellucida thereby facilitating hatching. We hypothesized that the impaired hatching of PPARδ−/− embryos is a result of decreased cell proliferation. To test this hypothesis, we compared the BrdU uptake by WT and PPARδ−/− embryos. The number of BrdU-positive cells was greatly reduced in PPARδ−/− embryos (FIG. 11*a*). Cell numbers per embryos were also markedly reduced in PPARδ−/− embryos (FIG. 11*b*).

Stimulation of Embryo Hatching by PPARδ Ligands.

Figure 12A:
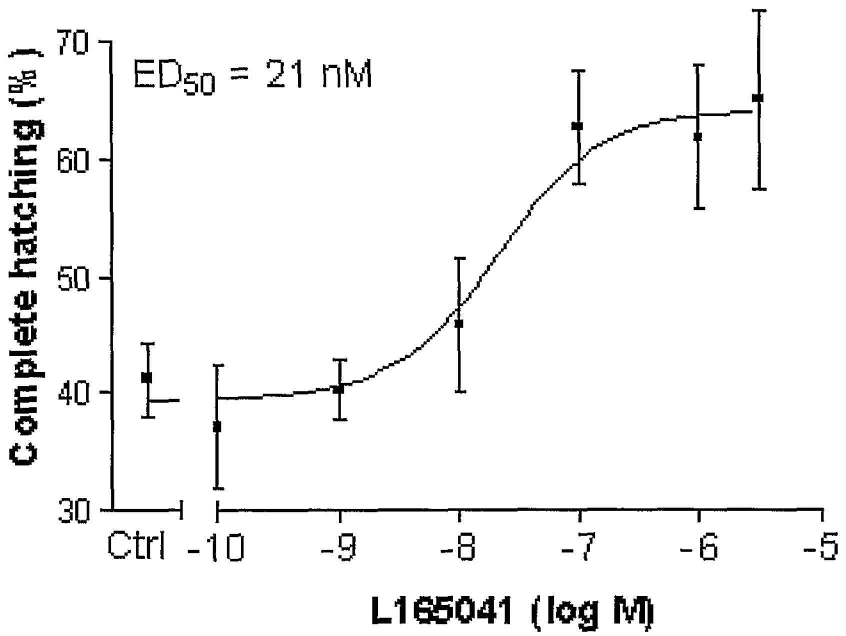
FIG. 12. L-165041 enhances embryo hatching. (a) Concentration-dependent stimulation of complete embryo hatching by L-165041. Wild type embryos were cultured in various concentrations of L-165041 beginning at two-cell stage. The proportions of embryos that hatched completely were determined 96 h later. The figure is based on three to six experiments, each of which used 15-20 embryos; the error bars depict the mean±S.D. (b) PPARδ ligand (L-165041, 1 μM), but neither PPARα (WY14643, 1 μM) nor PPARγ (Ciglitazone, 1 μM) ligand, enhanced complete embryo hatching. The figure depicts the combined results of one to two independent experiments each using 15-20 embryos. The numbers in the parentheses denote the numbers of completely hatched embryos versus total embryos. (c) L-165041 (1 μM) enhanced the hatching of two-cell, eight-cell, and morula staged embryos but not blastocyst staged embryos. The figure depicts the combined results of two to four independent experiments each using 14-20 embryos. The numbers in the parentheses denote the numbers of completely hatched embryos versus total embryos. (d) L-165041 increased embryonic cell proliferation. The figure depicts the result of one representative experiment using 24 control and 31 L-165041 treated wild type embryos. The experiment was repeated twice; the results were similar. * denotes $p<0.05$, ** denotes $p<0.01$.
Figure 12B:
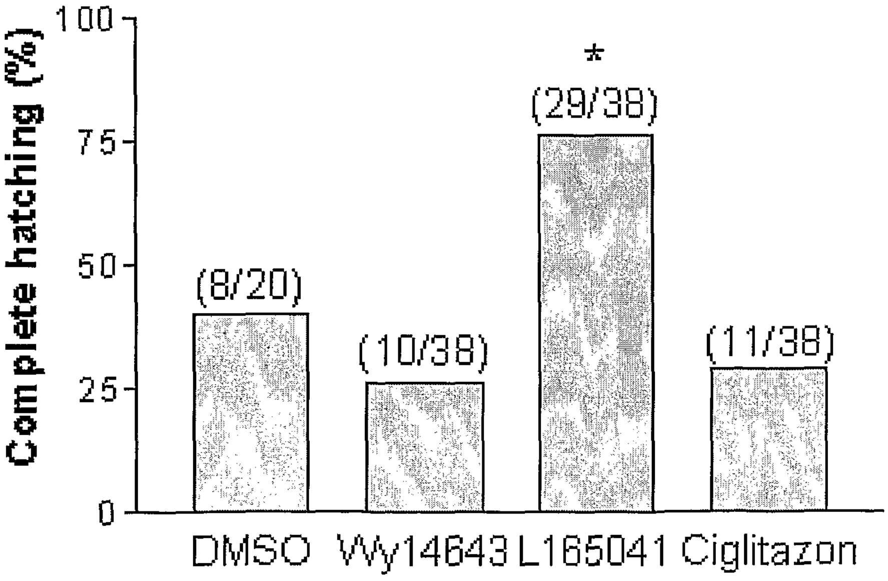
Figure 12C:
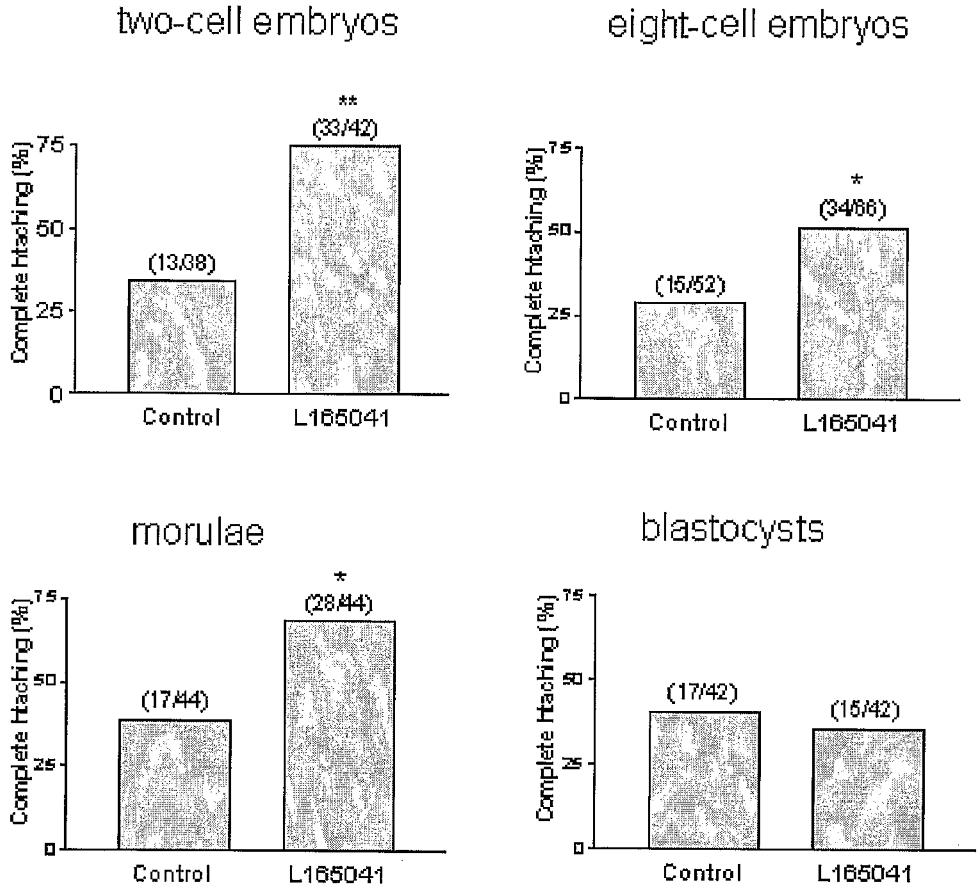
Figure 12D:
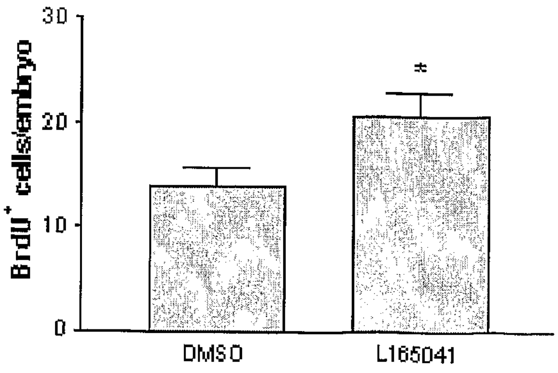

Both iloprost and L-165041 increased WT embryo hatching to a similar extent (FIG. 10). Their stimulatory effects were abrogated by PPARδ deletion (FIG. 10). L-165041 increased the percentage of hatched embryos in a concentration-dependent manner with an ED50 value of 21 nM (FIG. 12*a*). Neither Wy14,643, a PPARα ligand, nor ciglitazone, a PPARγ agonist, stimulated embryo hatching (FIG. 12*b*). L-165041 was effective in stimulating embryo hatching when it was added to embryos at two-cell, eight-cell or morula stage (FIG. 12*c*). Once a majority of embryos reached the blastocyst stage, the addition of L-165041 to the cultured medium was no longer effective in stimulating hatching (FIG. 12*c*). It has been proposed that embryo hatching occurs when the cells in blastocysts reach a critical number (Montag et al., 2000). Therefore, we determined the extent to which L-165041 enhanced embryonic cell proliferation. L-165041 (10 μM) increased the percentages of BrdU-positive cells over the untreated control (FIG. 12*d*). Taken together, these results indicate that exogenous PPARδ ligands such as L-165041 and iloprost accelerate hatching by stimulating the cell proliferation in embryos.

Regulation of Embryo Implantation by PPARδ

Figure 13A:
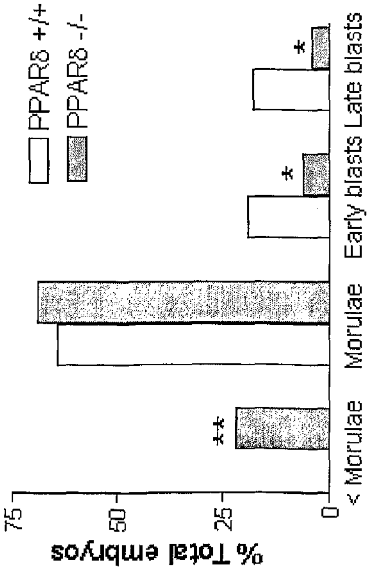
FIG. 13. PPARδ activation enhances the implantation of cultured embryos. Ninety-seven PPARδ+/+ and 54 PPARδ−/− embryos at two-cell stage were cultured for 48 h. The embryos were transferred to gestational carriers after their developmental stages were recorded. The numbers of gestation sacs were determined 72 h later. Significantly fewer PPARδ−/− embryos developed to blastocysts (a). When transferred to carriers, PPARδ−/− embryos had significantly lower implantation rates (b). Fifty-six and 42 PPARδ+/+embryos received DMSO and L165041, respectively, for 48 h beginning at two-cell stage. After stages of development were recorded, the embryos were transferred to gestational carriers. The numbers of gestation sacs were determined 72 h later. The extent of embryo development was similar in both groups at the time of embryo transfer (c). However, L-165041-treated embryos had significantly higher implantation rates (d). Numbers in the parentheses refer to the number of gestation sacs and the number of embryos transferred. * denotes $p<0.05$, ** denotes $p<0.01$.
Figure 13B:
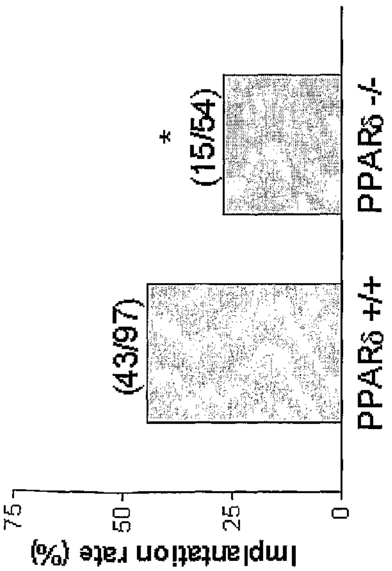
Figure 13C:
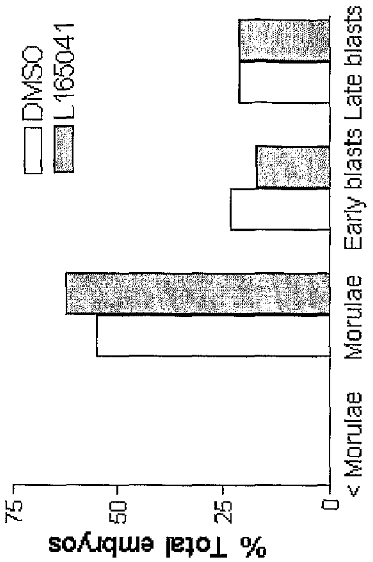
Figure 13D:
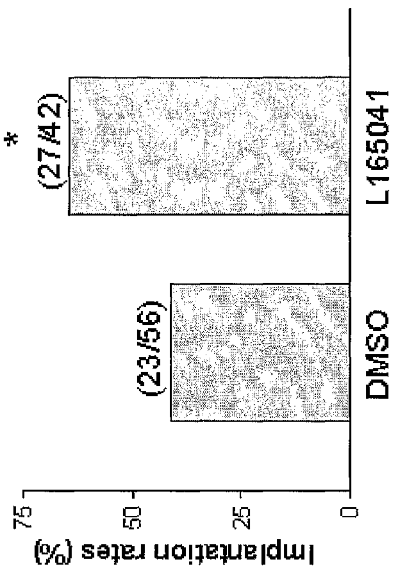

To determine the extent to which PPARδ is involved in implantation, two-cell embryos obtained from WT and PPARδ−/− mice were cultured for 48 h, enumerated and transferred to receptive uteri of gestational carriers. Gestation sacs were counted 72 h later. Numbers of early and late blastocysts developed from two-cell staged PPARδ−/− embryos were significantly lower than those developed from WT embryos (FIG. 13*a*). The implantation rate for PPARδ−/− embryos was also significantly lower than that for WT embryos (28% vs. 44%, $p<0.05$) (FIG. 13*b*). We next determined the extent to which pretreatment of two-cell embryos with L-165041 influences implantation rate. Two-cell embryos from WT mice were treated with L-165041 for 48 h. Embryos were enumerated and transferred to gestational carriers. Implantation rate was evaluated 72 h later. Although L-165041 did not significantly enhance blastocyst formation (FIG. 13*c*), it significantly increased the implantation rate (64% vs. 41%, $p<0.05$) (FIG. 13*d*). These results indicate that embryo PPARδ plays an important role in implantation. Exogenous PPARδ ligands promote implantation without altering blastocyst formation.

Discussion—Section II.

Our study suggests that embryo development and hatching requires PPARδ. Two-cell embryos from PPARδ−/− mice are capable of developing into blastocysts but the rate of blastocyst formation lags behind that of WT embryos. PPARδ is especially fundamental to blastocyst hatching. Compared with WT embryos, a significant number of two-cell PPARδ−/− embryos failed to hatch after 96 h in culture. It is worth mentioning that extending the culture duration to 120 h did not change the outcome as the majority of the blastocysts became collapsed during this period. It has been proposed that embryo hatching is mediated by two major factors: (1) a crucial cell number increase in embryos (Montag et al., 2000), which results in thinning of zona pellucida and (2) the digestion of zona by proteolytic enzymes (Sawada et al., 1990). Our results reveal that PPARδ mediates the proliferation embryonic cells and thereby increases embryonic cell mass. Compared with WT embryos, PPARδ−/− embryos exhibit very low BrdU incorporation. The cell numbers of PPARδ−/− embryos were only about 30% of those of WT embryos after 72 h in culture.

PPARδ is a nuclear receptor which binds a number of endogenous and synthetic ligands (Forman et al., 1997). Our previous study suggests that COX-2 derived PGI2 in embryos may be an endogenous PPARδ ligand. Ligand-activated PPARδ forms a heterodimer with retinoid X receptor (RXR) which binds PPAR response elements and activates gene transcription (Kliewer et al., 1994). A number of PPARδ-mediated genes have been reported and two of these genes, 14-3-3ε and phosphoinositide dependent kinase-1 (PDK-1), are involved in protecting cells from apoptosis (Di-Poi et al., 2002; Liou et al., 2006). However, the mechanism by which PPARδ promotes embryo cell proliferation is unknown. It was reported that over-expression of PPARδ in the vascular smooth muscle cells increases post-confluent cell proliferation by increasing cyclin A and CDK2 as well as decreasing p57kip2 (Zhang et al., 2002). It is possible that PPARδ-mediated 14-3-3 upregulation is involved in cell proliferation because 14-3-3 proteins are considered to be scaffolds for a large number of proteins, including signaling molecules and receptors (Fu et al., 2000; Tzivion and Avruch, 2002). Work is in progress to address this possibility. PPARδ may also play an important role in protecting embryo cells from apoptosis via 14-3-3ε (Liou et al., 2006) and PDK-1 (Di-Poi et al., 2002). It was reported that the inner cell mass (ICM) of blastocytes in culture are vulnerable to oxidative apoptosis (Brison and Schultz, 1997; Schratt et al., 2004). PGI2-activated PPARδ may protect ICM from apoptosis by upregulating 14-3-3ε, which sequesters Bad phosphorylated via the PDK-1 and Akt pathway (Datta et al., 1997; Zha et al., 1996). The anti-apoptotic function of PPARδ may contribute to increased cell numbers in blastocysts and enhanced hatching.

It has been reported that COX-2 derived PGI2 in the uterus is involved in embryo implantation, and PPARδ has been implicated for the action of PGI2 (Lim et al., 1999). The role of the embryo PPARδ in implantation has not been reported. Results from the present study provide direct evidence for a crucial role of embryo PPARδ in implantation. To mimic IVF procedures, we cultured WT and PPARδ−/− two-cell embryos in vitro for 48 h. Embryos at various stages of development were counted and transferred to receptive gestational carriers. Gestation sacs in the uterus were counted 72 h later. The number of gestation sacs from PPARδ−/− embryos was significantly less than that from WT embryos. Reduced implantation of PPARδ−/− embryos is correlated with the retarded embryo development and blastocyst formation of PPARδ−/− embryos. These results underscore the importance of PPARδ-mediated, enhanced cell proliferation in promoting the growth, maturation (hatching) and implantation of preimplantation embryos.

A major goal of our studies is to improve IVF. We have previously reported that iloprost, a stable PGI2 analog, enhances embryo implantation and the potential of live birth (Huang et al., 2004b). In the present study, we confirmed the previous data and shed light on the mechanism by which exogenous iloprost enhances embryo hatching and implantation. Our results show that PPARδ is the target of PGI2 in the preimplantation embryos. Enhanced blastocyst hatching by iloprost was completely abrogated in PPARδ−/− embryos. A synthetic PPARδ ligand, L-165041, exerted an effect similar to that of iloprost, but a combination of iloprost with L-165041 did not have additional effects. These results further suggest that endogenous PGI2 production in cultured embryos is limited and that exogenous PGI2 analog or synthetic PPARδ ligand can further activate PPARδ. PPARδ activation by synthetic ligand or PGI2 analog (iloprost) promotes further cell proliferation resulting in a higher hatching rate. It is worth noting that the effect of L-165041 is not limited to two-cell-staged embryos. L-165041 was quite effective in enhancing embryo hatching even in morula-staged embryos. However, L-165041 did not appear to be effective in blastocyst-staged embryos. The afore-mentioned result is probably because some blastocysts had advanced development and were ready to hatch. This observation is of practical importance with respect to the timing of supplementing media with iloprost or PPARδ ligands. Naturally, the application of PPARδ ligands in human IVF requires a thorough investigation of its safety profiles.

L-165041 appears to enhance embryo implantation by a mechanism independent of its effect on blastocyst formation, because the developmental stages of control and experimental embryos at the time of embryos transfer were similar, yet transferred experimental embryos resulted in more gestation sacs. The molecular basis for the delayed action is unclear. We speculate that L-165041 induces a sustained signaling activation via PPARδ to enhance implantation. There probably is a crosstalk between the transcriptional signalings of uterine and embryo PPARδ. The coordination between embryo development and endometrial decidualization ensures a successful implantation. Elucidation of the molecular mechanism(s) will have major impacts on our understanding of embryo implantation and the potential to improve IVF success.

In summary, preimplantation embryos express PPARδ, which plays an essential role in embryo development, blastocyst formation, embryo hatching and implantation. Activation of embryo PPARδ is a novel therapeutic strategy to improve the outcome of IVF

TABLE I

Developmental Stages of PPARδ+/+ and PPARδ−/− embryos Over the Course of 96-hour Culture

| Developmental | PPARδ+/+ (n = 28) | | | PPARδ−/− (n = 51) | | |
|---|---|---|---|---|---|---|
| stages | 48 h | 72 h | 96 h | 48 h | 72 h | 96 h |
| <morula[§] | 1 (4)[+] | 0 (0) | 0 (0) | 6 (12) | 11 (22) | 15 (29) |
| morula | 11 (39) | 0 (0) | 0 (0) | 40 (78) | 21 (41) | 3 (6) |
| blastocyst | **14 (50) | *13 (46) | 4 (14) | 5 (10) | 12 (24) | 19 (37) |
| hatching[§] | 2 (7) | **15 (54) | **18 (64) | 0 (0) | 7 (14) | 12 (24) |
| hatched[§] | 0 (0) | 0 (0) | *6 (21) | 0 (0) | 0 (0) | 2 (4) |

[+]Numbers in parenthesis denote percentages

[§]<morula stage refers to two-cell, four-cell, and eight-cell staged embryos hatching refers to hatching blastocysts hatched refers to completely hatched blastocysts

*denotes $p < 0.05$,

**denotes $p < 0.01$ versus PPARδ−/− embryos

REFERENCES

Adderley, S. R., and Fitzgerald, D. J. (1999) Oxidative damage of cardiomyocytes is limited by extracellular regulated kinases ½-mediated induction of cyclooxygenase-2 *J Biol Chem.* 274, 5038-46.

Barak, Y., Liao, D., He, W., Ong, E. S., Nelson, M. C., Olefsky, J. M., Boland, R. and Evans, R. M. (2002) Effects of peroxisome proliferator-activated receptor delta on placentation, adiposity, and colorectal cancer. *Proc Natl Acad Sci USA,* 99, 303-308.

Berger, J. and Moller, D. E. (2002) The mechanisms of action of PPARs. *Annu Rev Med,* 53, 409-435.

Braissant, O. and Wahli, W. (1998) Differential Expression of Peroxisome Proliferator-Activated Receptor-{alpha}, -{beta}, and -{gamma} during Rat Embryonic Development. *Endocrinology,* 139, 2748-2754.

Brison, D. R., and Schultz, R. M. (1997) Apoptosis during mouse blastocyst formation: evidence for a role for survival factors including transforming growth factor alpha. *Biol Reprod.* 56, 1088-96.

Cheng, Y., Austin, S. C., Rocca, B., Koller, B. H., Coffman, T. M., Grosser, T., Lawson, J. A., and FitzGerald, G. A. (2002) Role of prostacyclin in the cardiovascular response to thromboxane A2. *Science.* 296, 539-41.

Cutler, N. S., Graves-Deal, R., LaFleur, B. J., Gao, Z., Boman, B. M., Whitehead, R. H., Terry, E., Morrow, J. D. and Coffey, R. J. (2003) Stromal production of prostacyclin confers an antiapoptotic effect to colonic epithelial cells. *Cancer Res,* 63, 1748-1751.

Datta, S. R., Dudek, H., Tao, X., Masters, S., Fu, H., Gotoh, Y., and Greenberg, M. E. (1997) Akt phosphorylation of BAD couples survival signals to the cell-intrinsic death machinery. *Cell.,* 91, 231-41.

Di-Poi, N., Tan, N. S., Michalik, L., Wahli, W., and Desvergne, B. (2002) Antiapoptotic role of PPARbeta in keratinocytes via transcriptional control of the Akt1 signaling pathway. *Mol Cell.* 10, 721-33.

Ding, N. Z., Teng, C. B., Ma, H., Ni, H., Ma, X. H., Xu, L. B. and Yang, Z. M. (2003) Peroxisome proliferator-activated receptor delta expression and regulation in mouse uterus during embryo implantation and decidualization. *Mol Reprod Dev,* 66, 218-224.

Forman, B. M., Chen, J. and Evans, R. M. (1997) Hypolipidemic drugs, polyunsaturated fatty acids, and eicosanoids are ligands for peroxisome proliferator-activated receptors alpha and delta. *Proc Natl Acad Sci USA,* 94, 4312-4317.

Fu, H., Subramanian, R. R., and Masters, S. C. (2000) 14-3-3 proteins: structure, function, and regulation. *Annu Rev Pharmacol Toxicol.* 40, 617-47.

Gupta, R. A., Tan, J., Krause, W. F., Geraci, M. W., Willson, T. M., Dey, S. K. and DuBois, R. N. (2000) Prostacyclin-mediated activation of peroxisome proliferator-activated receptor delta in colorectal cancer. *Proc Natl Acad Sci USA,* 97, 13275-13280.

Hao, C. M., Redha, R., Morrow, J. and Breyer, M. D. (2002) Peroxisome proliferator-activated receptor delta activation promotes cell survival following hypertonic stress. *J Biol Chem,* 277, 21341-21345.

Hardy, K. (1997) Cell death in the mammalian blastocyst. *Mol Hum Reprod.* 3, 919-25.

Hihi, A. K., Michalik, L. and Wahli, W. (2002) PPARs: transcriptional effectors of fatty acids and their derivatives. *Cell Mol Life Sci,* 59, 790-798.

Huang, J. C., Arbab, F., Tumbusch, K. J., Goldsby, J. S., Matijevic-Aleksic, N. and Wu, K. K. (2002) Human Fallopian Tubes Express Prostacyclin (PGI) Synthase and Cyclooxygenases and Synthesize Abundant PGI. *J Clin Endocrinol Metab,* 87, 4361-4368.

Huang, J.-C., Wun, W.-S. A., Goldsby, J. S., Wun, I. C., Falconi, S. M. and Wu, K. K. (2003) Prostacyclin enhances embryo hatching but not sperm motility. *Hum. Reprod.,* 18, 2582-2589.

Huang, J. C., Goldsby, J. S., Arbab, F., Melhem, Z., Aleksic, N., and Wu, K. K. (2004a) Oviduct prostacyclin functions as a paracrine factor to augment the development of embryos. *Hum Reprod.* 19, 2907-12. Epub 2004 Oct. 18.

Huang, J.-C., Goldsby, J. S., and Wun, W.-S. A. (2004b) Prostacyclin enhances the implantation and live birth potentials of mouse embryos. *Hum. Reprod.,* 19, 1856-1860.

Huang, J. C., Wun, W. S., Goldsby, J. S., Matijevic-Aleksic, N., and Wu, K. K. (2004c) Cyclooxygenase-2-derived endogenous prostacyclin enhances mouse embryo hatching. *Hum Reprod.* 19, 2900-6. Epub 2004 Oct. 15.

Julan, L., Guan, H., van Beek, J. P. and Yang, K. (2005) Peroxisome proliferator-activated receptor delta suppresses beta-hydroxysteroid dehydrogenase type 2 gene expression in human placental trophoblast cells. *Endocrinology,* 146, 1482-1490. Epub 2004 December 1489.

Kliewer, S., Forman, B., Blumberg, B., Ong, E., Borgmeyer, U., Mangelsdorf, D., Umesono, K., and Evans, R. (1994) Differential Expression and Activation of a Family of Murine Peroxisome Proliferator-Activated Receptors. *PNAS.* 91, 7355-7359.

Kusam, S., Vasanwala, F. H. and Dent, A. L. (2004) Transcriptional repressor BCL-6 immortalizes germinal center-like B cells in the absence of p53 function. Oncogene, 23, 839-844.

Lee, C. H., Chawla, A., Urbiztondo, N., Liao, D., Boisvert, W. A., Evans, R. M. and Curtiss, L. K. (2003) Transcriptional repression of atherogenic inflammation: modulation by PPARdelta. *Science,* 302, 453-457. Epub 2003 September 2011.

Lim, H. and Dey, S. K. (2000) PPAR delta functions as a prostacyclin receptor in blastocyst implantation. *Trends Endocrinol Metab,* 11, 137-142.

Lim, H., Gupta, R. A., Ma, W. G., Paria, B. C., Moller, D. E., Morrow, J. D., DuBois, R. N., Trzaskos, J. M. and Dey, S. K. (1999) Cyclo-oxygenase-2-derived prostacyclin mediates embryo implantation in the mouse via PPARdelta. *Genes Dev,* 13, 1561-1574.

Liou, J.-Y., Matijevic-Aleksic, N., Cieslik, K., Lee, S., H-P, T. and K., W. K. (2004) Prostacyclin protects endothelial survival by PPAR delta-Mediated 14-3-3 upregulation. *FASEB,* 18, C97.

Liou, J. Y., Lee, S., Ghelani, D., Matijevic-Aleksic, N., and Wu, K. K. (2006) Protection of endothelial survival by peroxisome proliferator-activated receptor-delta mediated 14-3-3 upregulation. *Arterioscler Thromb Vasc Biol.,* 26, 1481-7. Epub 2006 Apr. 27.

Mangelsdorf, D. J., Thummel, C., Beato, M., Herrlich, P., Schutz, G., Umesono, K., Blumberg, B., Kastner, P., Mark, M., Chambon, P., et al. (1995) The nuclear receptor superfamily: the second decade. *Cell,* 83, 835-839.

Michalik, L., Desvergne, B., Tan, N. S., Basu-Modak, S., Escher, P., Rieusset, J., Peters, J. M., Kaya, G., Gonzalez, F. J., Zakany, J., et al. (2001) Impaired skin wound healing in peroxisome proliferator-activated receptor (PPAR)alpha and PPARbeta mutant mice. *J Cell Biol,* 154, 799-814.

Montag, M., Koll, B., Holmes, P. and van der Ven, H. (2000) Significance of the number of embryonic cells and the state of the zona pellucida for hatching of mouse blastocysts in vitro versus in vivo. *Biol Reprod,* 62, 1738-1744.

Namba, T., Oida, H., Sugimoto, Y., Kakizuka, A., Negishi, M., Ichikawa, A., and Narumiya, S. (1994) cDNA cloning of a mouse prostacyclin receptor. Multiple signaling pathways and expression in thymic medulla. *J Biol Chem.* 269, 9986-92.

Paria, B. C., Huet-Hudson, Y. M., and Dey, S. K. (1993) Blastocyst's state of activity determines the "window" of implantation in the receptive mouse uterus. *Proc Natl Acad Sci USA.* 90, 10159-62.

Peters, J. M., Lee, S. S., Li, W., Ward, J. M., Gavrilova, O., Everett, C., Reitman, M. L., Hudson, L. D. and Gonzalez, F. J. (2000) Growth, adipose, brain, and skin alterations resulting from targeted disruption of the mouse peroxisome proliferator-activated receptor beta(delta). *Mol Cell Biol,* 20, 5119-5128.

Sawada, H., Yamazaki, K., and Hoshi, M. (1990) Trypsin-like hatching protease from mouse embryos: evidence for the presence in culture medium and its enzymatic properties. *J Exp Zool.* 254, 83-7.

Schratt, G., Philippar, U., Hockemeyer, D., Schwarz, H., Alberti, S., and Nordheim, A. (2004) SRF regulates Bcl-2 expression and promotes cell survival during murine embryonic development. *Embo J.,* 23, 1834-44. Epub 2004 Apr. 1.

Shaffer, A. L., Yu, X., He, Y., Boldrick, J., Chan, E. P. and Staudt, L. M. (2000) BCL-6 represses genes that function in lymphocyte differentiation, inflammation, and cell cycle control. *Immunity,* 13, 199-212.

Shi, Y., Hon, M. and Evans, R. M. (2002) The peroxisome proliferator-activated receptor delta, an integrator of transcriptional repression and nuclear receptor signaling. *Proc Natl Acad Sci USA,* 99, 2613-2618. Epub 2002 February 2626.

Tan, N. S., Michalik, L., Noy, N., Yasmin, R., Pacot, C., Heim, M., Fluhmann, B., Desvergne, B. and Wahli, W. (2001) Critical roles of PPAR beta/delta in keratinocyte response to inflammation. *Genes Dev,* 15, 3263-3277.

Tzivion, G., and Avruch, J. (2002) 14-3-3 proteins: active cofactors in cellular regulation by serine/threonine phosphorylation. *J Biol Chem.,* 277, 3061-4. Epub 2001 Nov. 14.

Yeung, W. S., Ho, P. C., Lau, E. Y., and Chan, S. T. (1992) Improved development of human embryos in vitro by a human oviductal cell co-culture system. *Hum Reprod.* 7, 1144-9.

Wahli, W. (2002) Peroxisome proliferator-activated receptors (PPARs): from metabolic control to epidermal wound healing. *Swiss Med Wkly,* 132, 83-91.

Willson, T. M., Brown, P. J., Sternbach, D. D. and Henke, B. R. (2000) The PPARs: from orphan receptors to drug discovery. *J Med Chem,* 43, 527-550.

Zha, J., Harada, H., Yang, E., Jockel, J., and Korsmeyer, S. J. (1996) Serine phosphorylation of death agonist BAD in response to survival factor results in binding to 14-3-3 not BCL-X(L). *Cell.* 87, 619-28.

Zhang, J., Fu, M., Zhu, X., Xiao, Y., Mou, Y., Zheng, H., Akinbami, M. A., Wang, Q., and Chen, Y. E. (2002). Peroxisome proliferator-activated receptor delta is up-regulated during vascular lesion formation and promotes post-confluent cell proliferation in vascular smooth muscle cells. J Biol Chem 277, 11505-11512.

Xu, J., Cheung, T. M., Chan, S. T., Ho, P. C. and Yeung, W. S. (2000) Human oviductal cells reduce the incidence of apoptosis in cocultured mouse embryos. *Fertil Steril,* 74, 1215-1219

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. The disclosures of all patents, patent applications and publications cited herein are hereby incorporated herein by reference, to the extent that they provide procedural or other details supplementary to those set forth herein.

What is claimed is:

1. An in vitro method of activating a peroxisome proliferator activated receptor δ (PPARδ) in a preimplantation mammalian embryo, comprising:

1) culturing said embryo in an embryo culture medium to form an in vitro cultured embryo;
2) adding a non-prostaglandin PPARδ ligand to said cultured embryo in vitro, wherein said ligand is added upon or after commencement of expression of PPARδ in the cells of the embryo; and
3) binding said non-prostaglandin PPARδ ligand to the expressed PPARδ to deter apoptosis in the cells of a cultured embryo and/or to increase proliferation of the cells of the cultured embryo in vitro.

2. The method of claim 1 wherein binding PPARδ ligand to said PPARδ enhances hatching of the embryo.

3. The method of claim 2 further comprising supplementing the medium with a prostaglandin, or analog thereof, in an amount effective to promote complete hatching of the embryo.

4. The method of claim 1 wherein said ligand further comprises at least one additional natural or synthetic PPARδ ligand.

5. The method of claim 1 wherein said ligand is added to said medium at the morula-stage or later in the development of said embryo.

6. The method of claim 1 wherein said ligand comprises GW501516.

7. The method of claim 1 wherein said method yields an embryo with increased in vivo implantation potential.

8. The method of claim 1 wherein said method yields an embryo with enhanced potential for establishment of a viable pregnancy.

9. The method of claim 1, wherein said embryo culture medium comprises said non-prostaglanding PPARδ ligand in an amount effective to increase the proliferation of the cells of the embryo.

* * * * *

UNITED STATES PATENT AND TRADEMARK OFFICE

CERTIFICATE OF CORRECTION

PATENT NO. : 8,632,452 B2
APPLICATION NO. : 12/090060
DATED : January 21, 2014
INVENTOR(S) : Huang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1295 days.

Signed and Sealed this
Twenty-second Day of September, 2015

Michelle K. Lee
*Director of the United States Patent and Trademark Office*